United States Patent [19]

Berry et al.

[11] Patent Number: 5,779,696

[45] Date of Patent: Jul. 14, 1998

[54] METHOD AND APPARATUS FOR PERFORMING CORNEAL RESHAPING TO CORRECT OCULAR REFRACTIVE ERRORS

[75] Inventors: Michael J. Berry, Carmel; David R. Hennings, New Castle; Arthur V. Vassiliadis, Los Altos, all of Calif.

[73] Assignee: Sunrise Technologies International, Inc., Fremont, Calif.

[21] Appl. No.: 429,744

[22] Filed: Apr. 26, 1995

Related U.S. Application Data

[60] Division of Ser. No. 160,405, Dec. 2, 1993, abandoned, which is a continuation-in-part of Ser. No. 702,960, May 20, 1991, abandoned, which is a continuation-in-part of Ser. No. 556,886, Jul. 23, 1990, abandoned, and Ser. No. 596,060, Oct. 11, 1990, abandoned.

[51] Int. Cl.$^6$ .................................................. A61N 5/06
[52] U.S. Cl. ................................ 606/16; 606/3; 606/5; 606/10; 606/13
[58] Field of Search ................ 606/2, 3–18; 607/88–92

[56] References Cited

U.S. PATENT DOCUMENTS 5,437,658  8/1995  Muller et al. .............................. 606/5

FOREIGN PATENT DOCUMENTS

| 190829 | 8/1986 | European Pat. Off. . |
| 8705496 | 9/1987 | WIPO . |
| 9105515 | 5/1991 | WIPO . |

OTHER PUBLICATIONS

Schröder et al; "An Ophthalmic Excimer Laser for Corneal Surgery"; Am J. Ophthal. vol. 103, No. 3 Mar. 1987 pp. 472–473.

Taboila et al; "Optically Coupled Technique for Photorefractive Surgery of the Cornea; Optics Letters"; vol 15; No. 9; May 1, 1990; pp. 458–460.

Seiler et al. "Laser Thermokeratoplasty by Means of a Pulsed Holmuim: YAG Laser for Hyperopic Correction" Refractive & Corneal Surg. vol. 6 pp. 338–339 Sep./Oct. 1990.

Valderrama et al "Chemical Laser Interactions with Human Corneal Tissue"; SPIE vol. 1064 Thermal & Optical Interact with Biol & Related Composite Materials (1989) pp. 135–145.

*Primary Examiner*—David Shay
*Attorney, Agent, or Firm*—Majestic, Parsons, Siebert & Hsue

[57] ABSTRACT

A noninvasive method is described for performing accurate and controlled reshaping of the anterior surface of the cornea in order to correct ocular refractive errors such as myopia (nearsightedness), hyperopia (farsightedness), and astigmatism. The invention uses a light source emitting a wavelength or wavelengths with correct optical penetration depth (s) to induce changes in corneal stromal collagen without damaging the corneal endothelium, together with a light delivery and control means for producing the required irradiance, exposure time, and geometric pattern, in order to achieve the desired change in corneal shape. Corneal shape is monitored before, during, and after the procedure by a corneal topography system. Anterior corneal surface cooling by a transparent heat sink is used to prevent damage to the epithelium and to Bowman's layer.

9 Claims, 11 Drawing Sheets

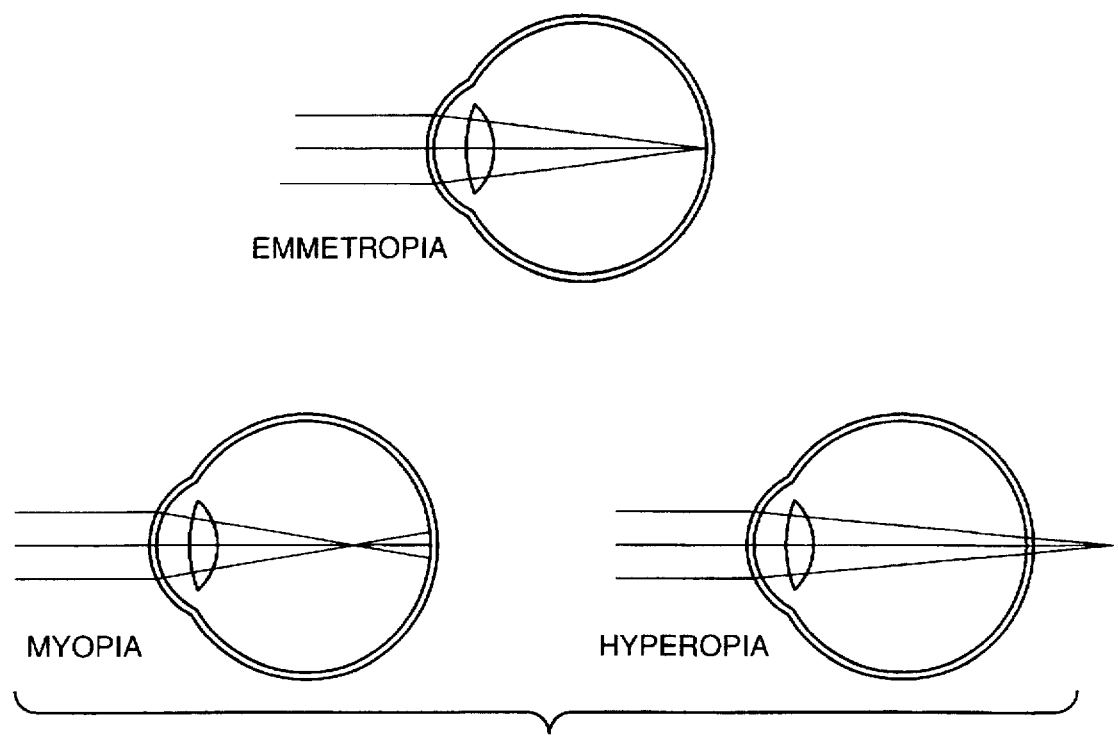
FIG._1
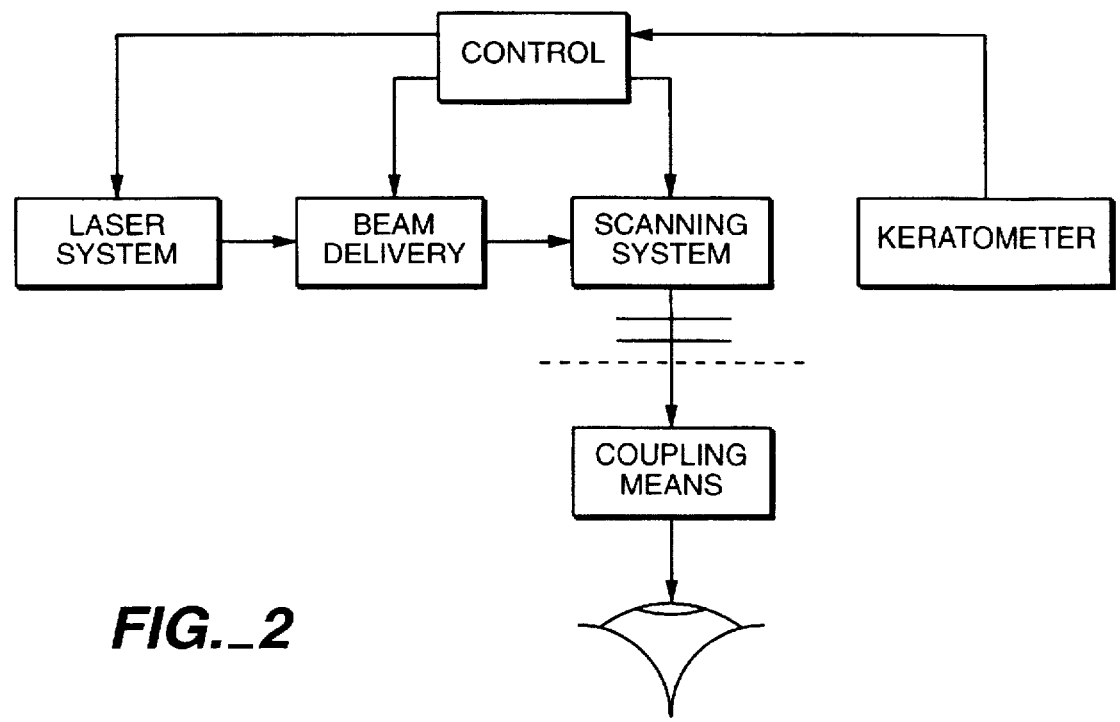
FIG._2

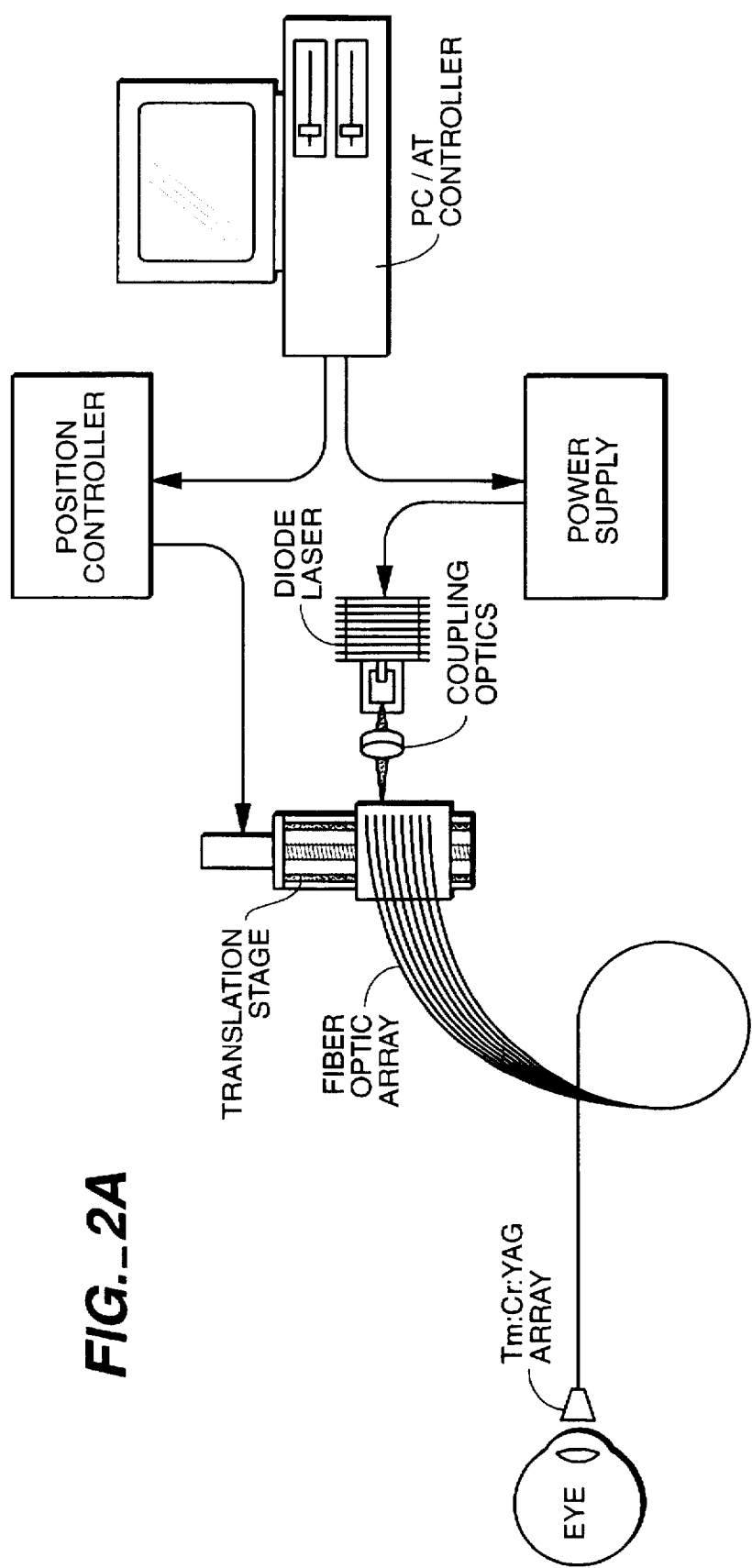
FIG._2A

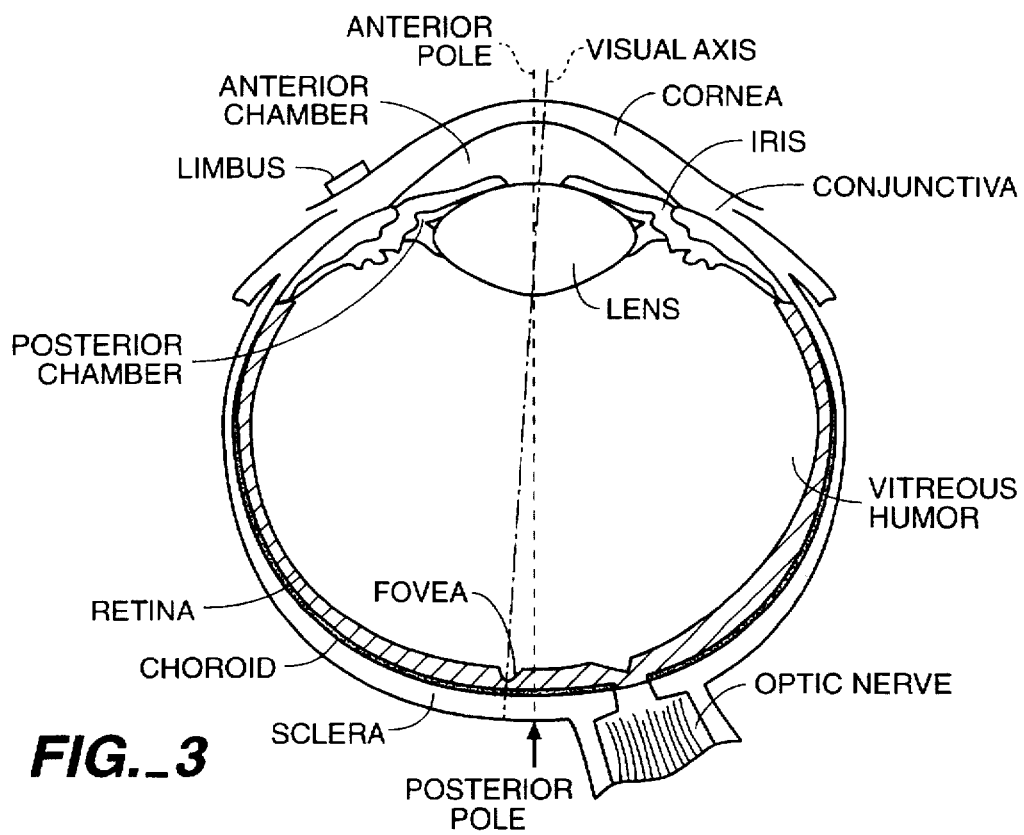
FIG._3
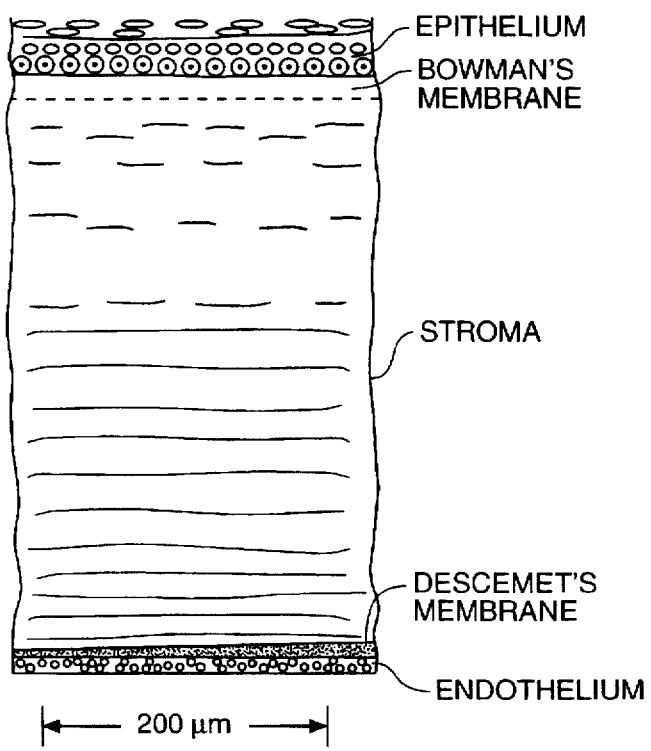
FIG._4

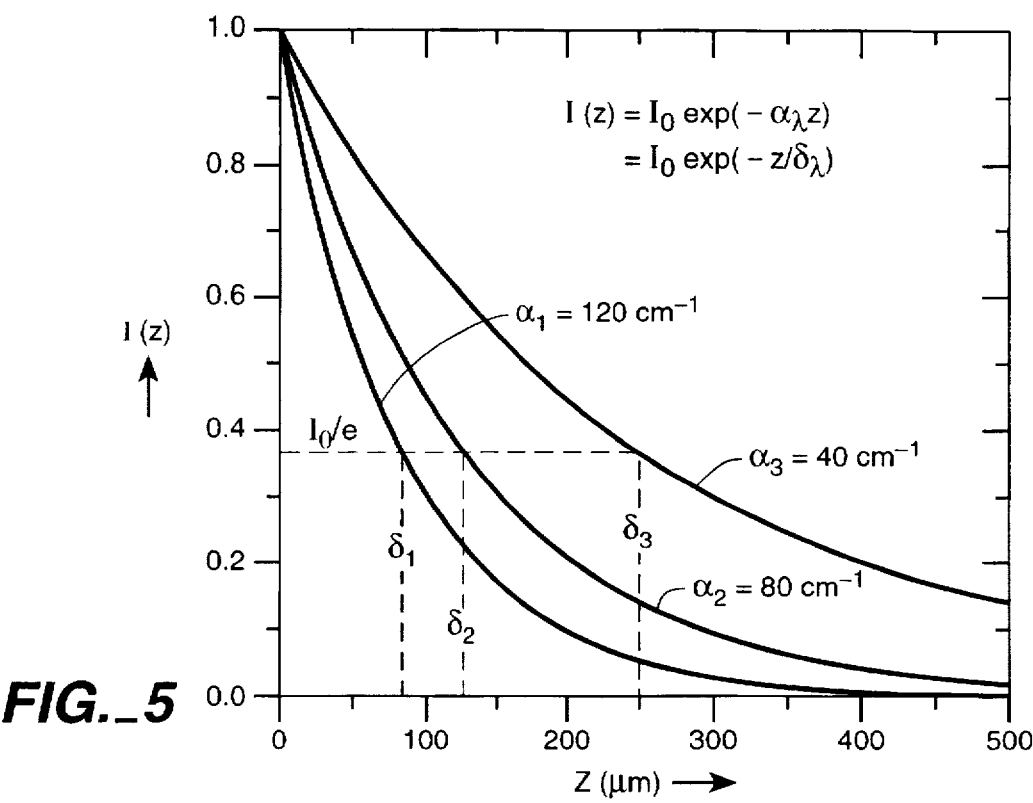
*FIG._5*
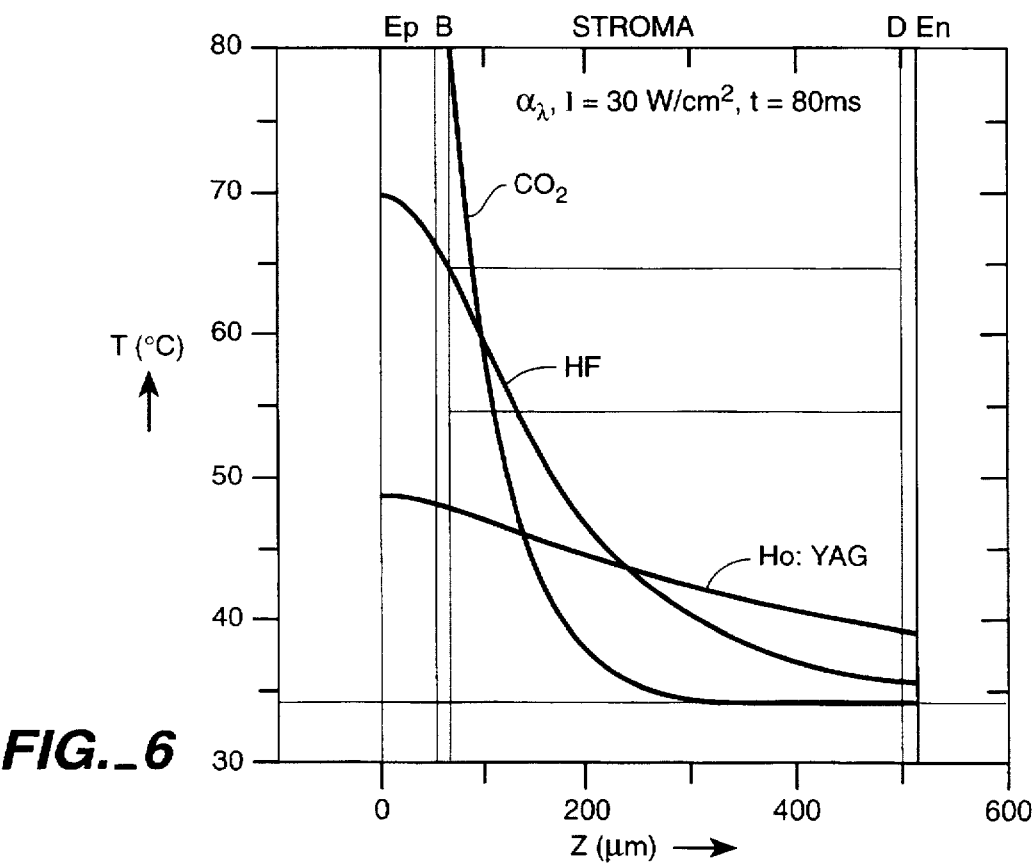
*FIG._6*

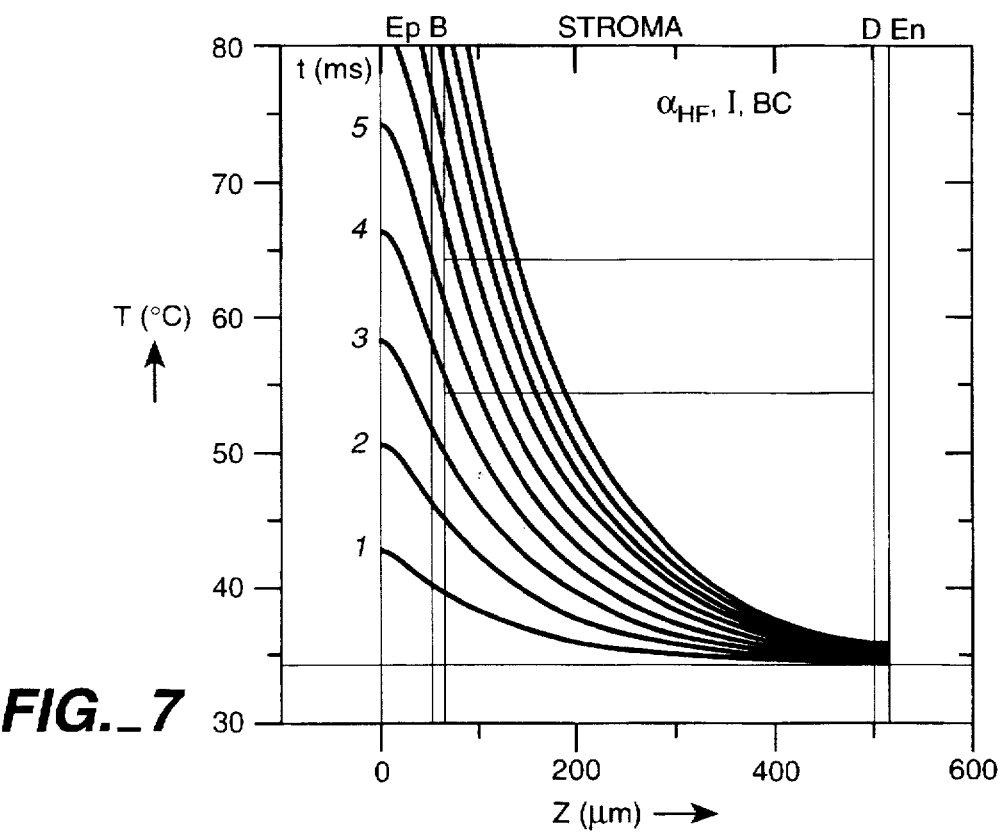
FIG._7
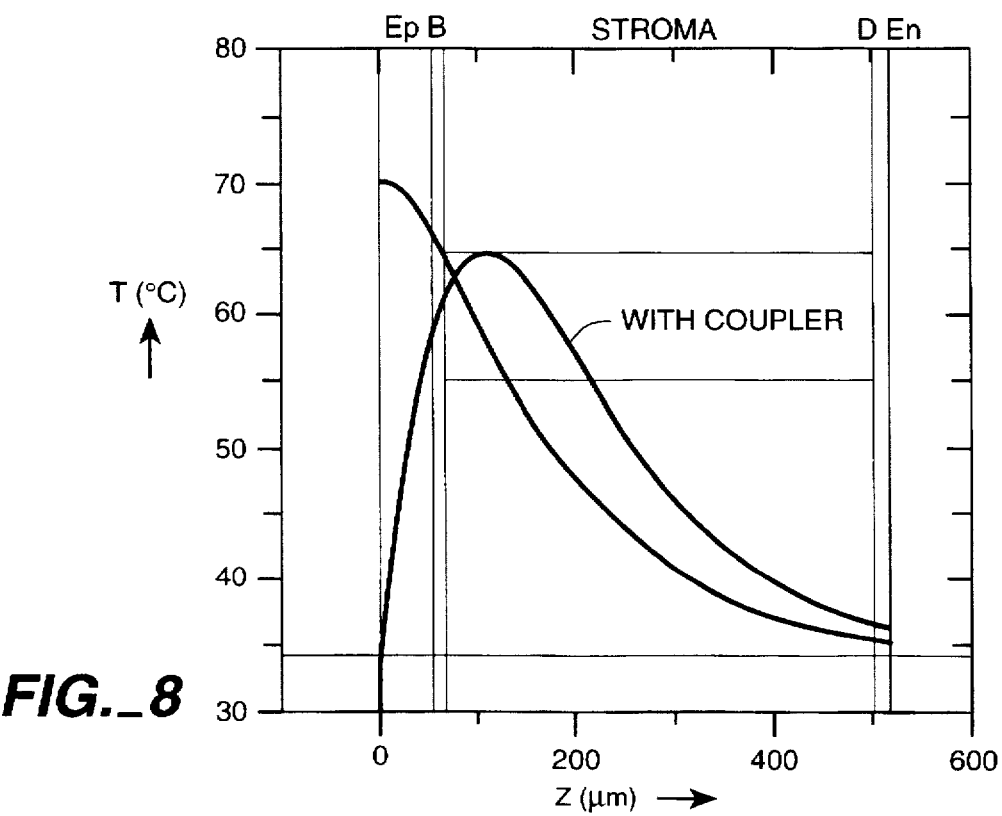
FIG._8

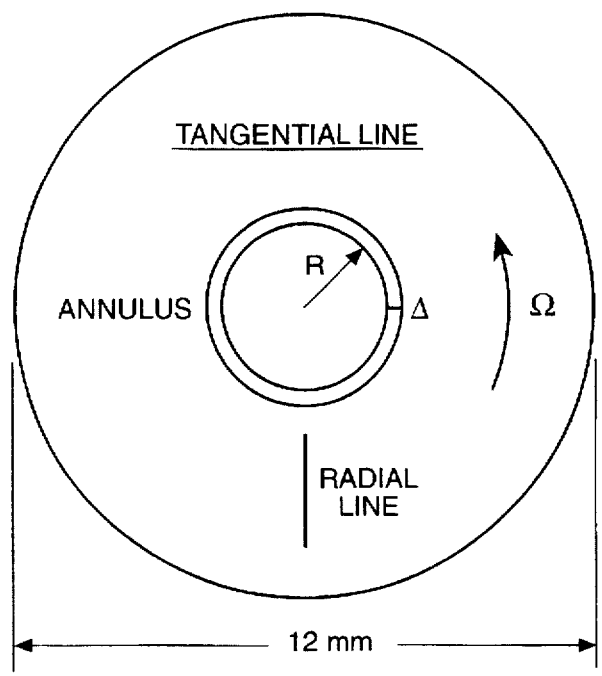
FIG._9
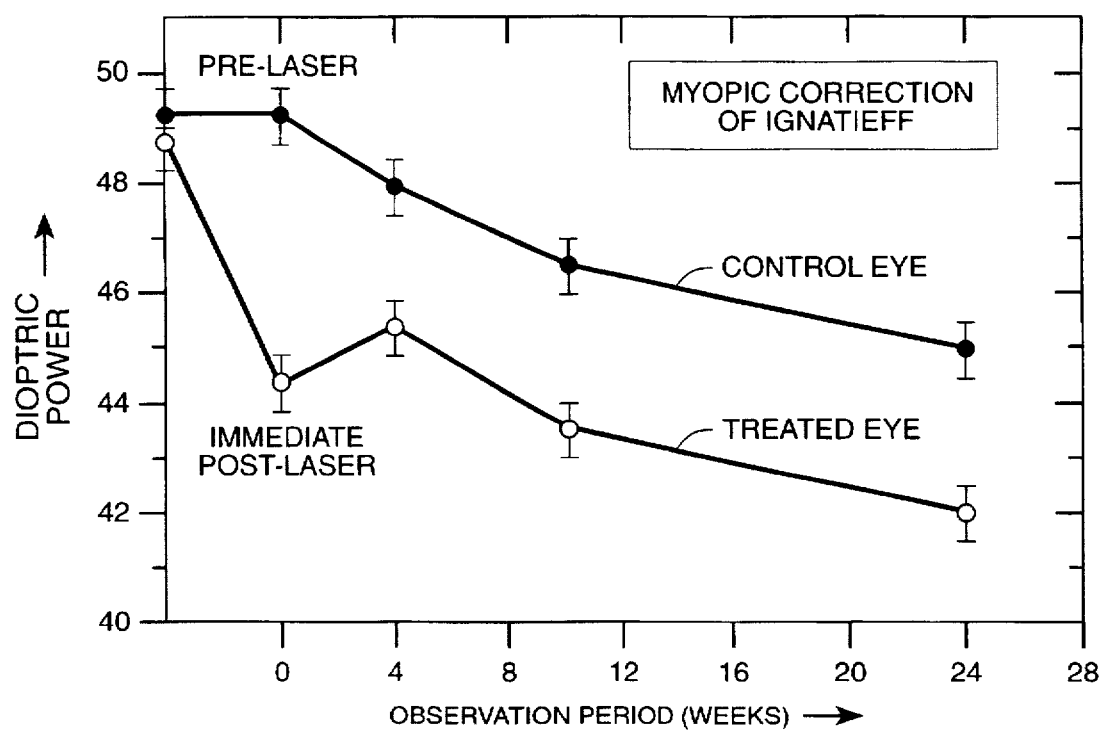
FIG._10

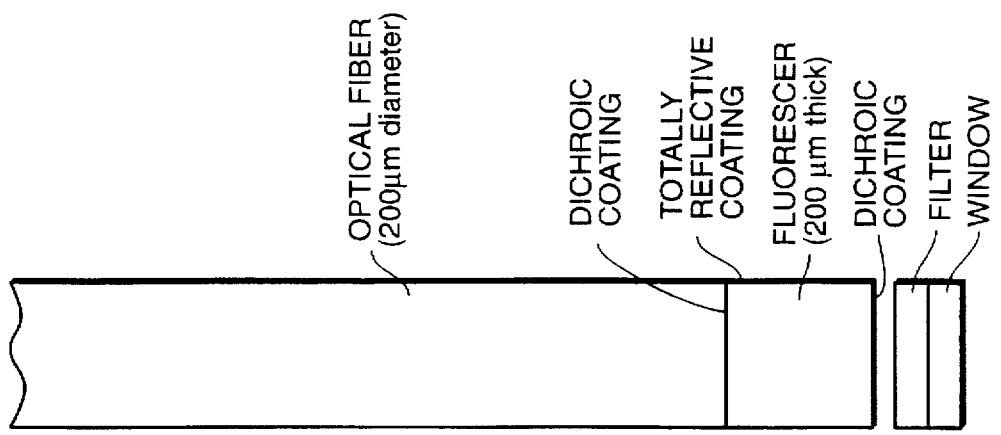
FIG._12
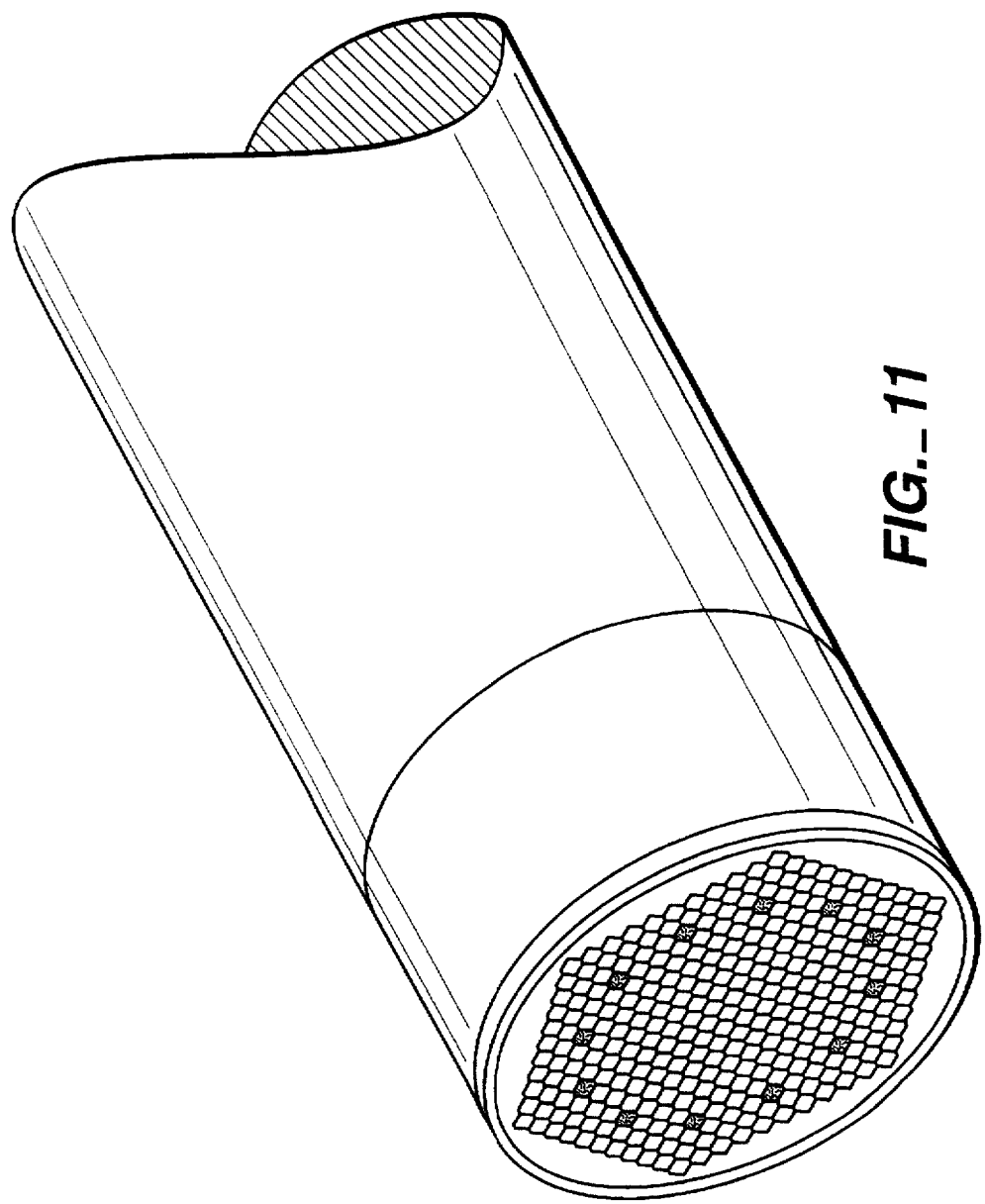
FIG._11

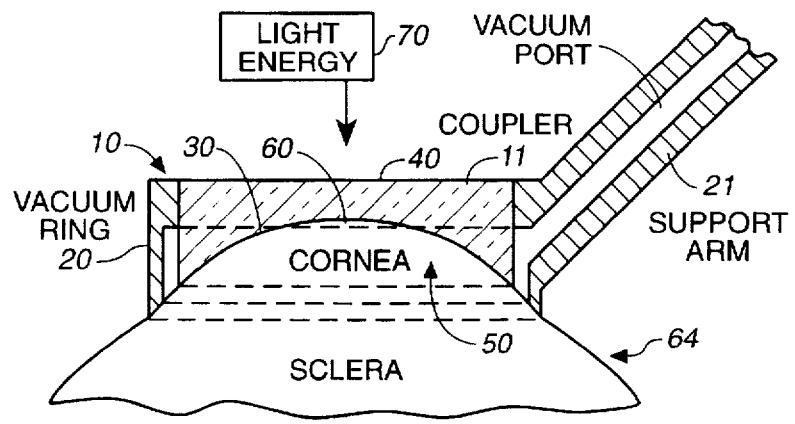
FIG._13
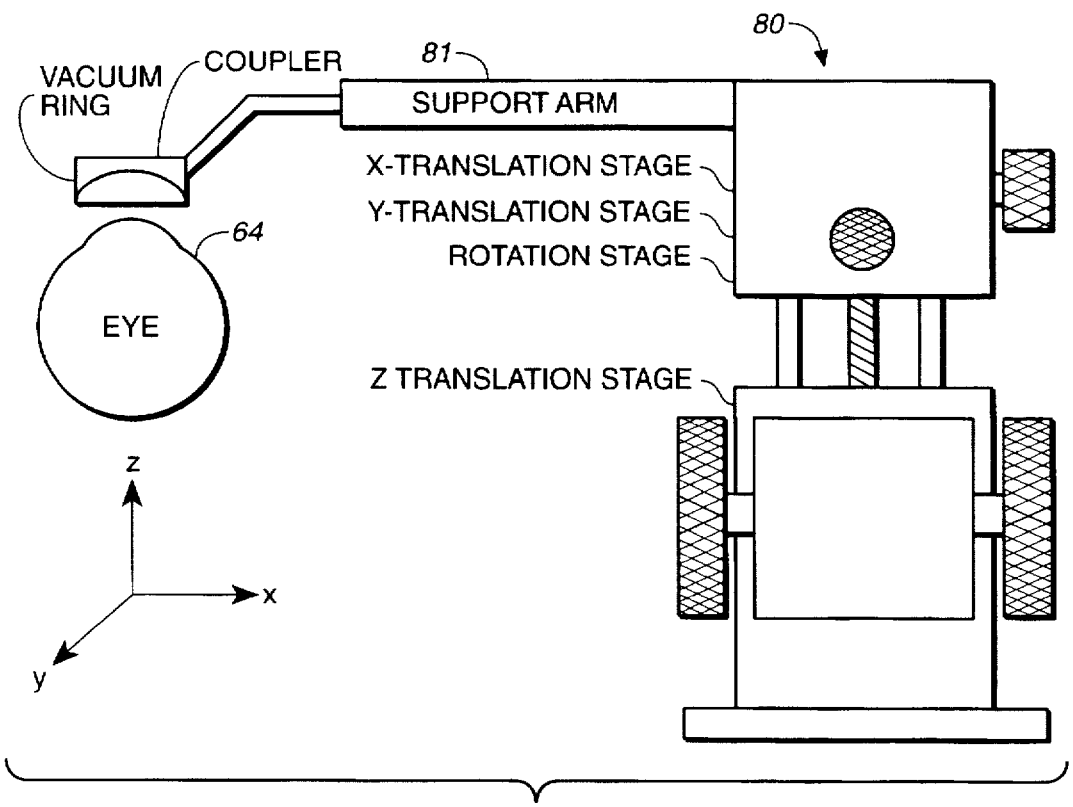
FIG._14

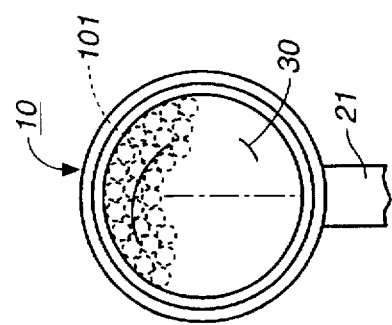
FIG._16
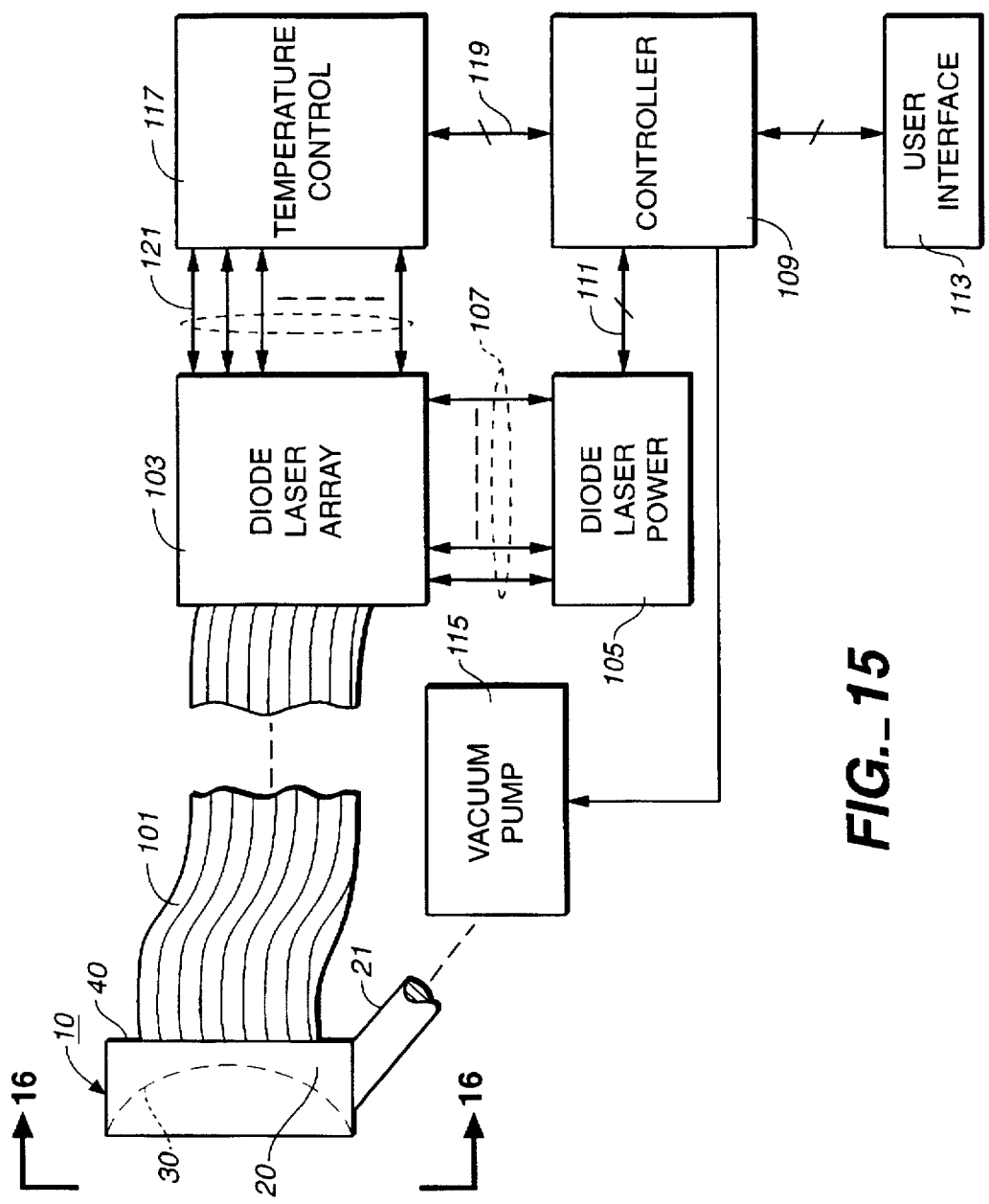
FIG._15

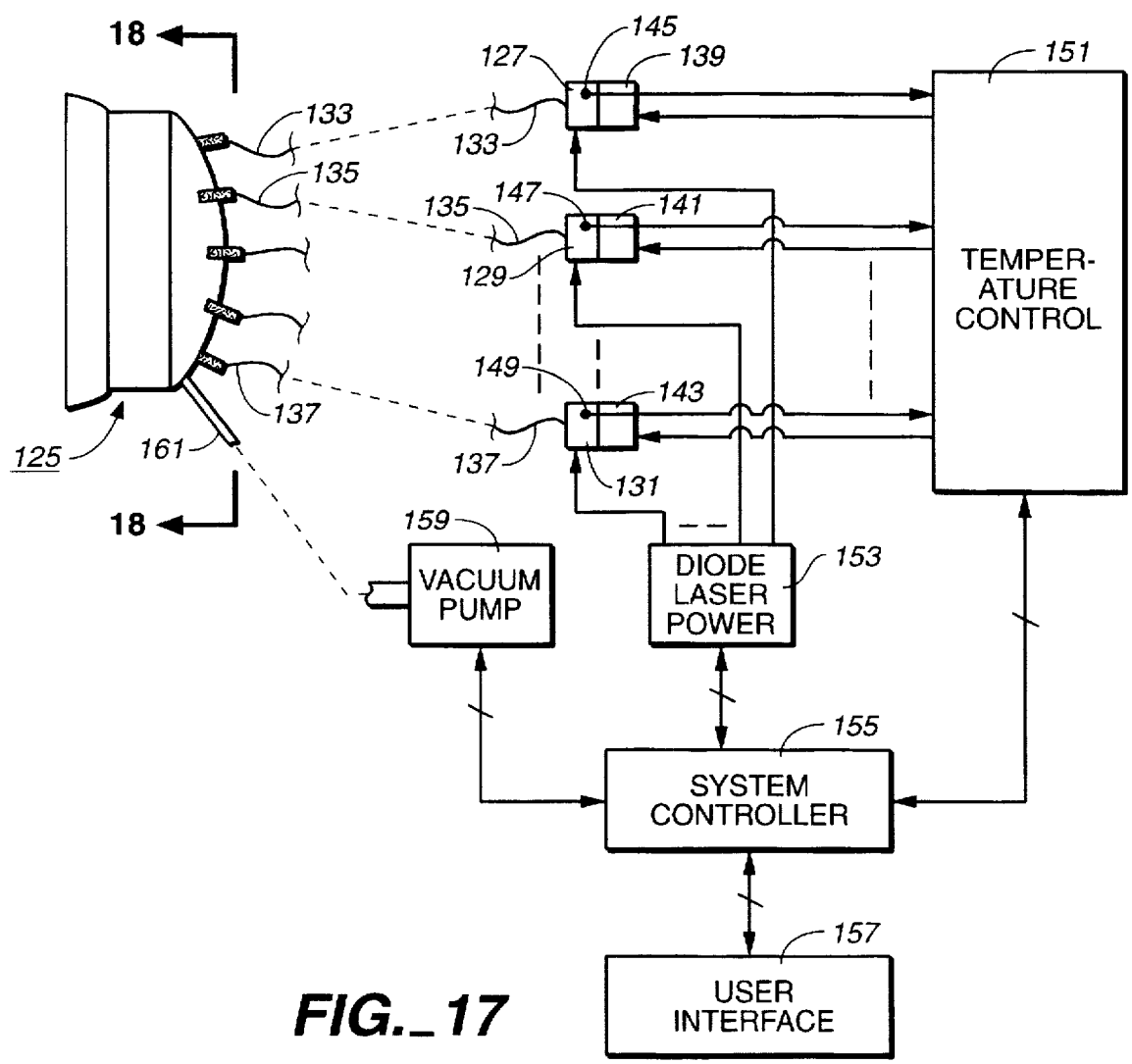
FIG._17
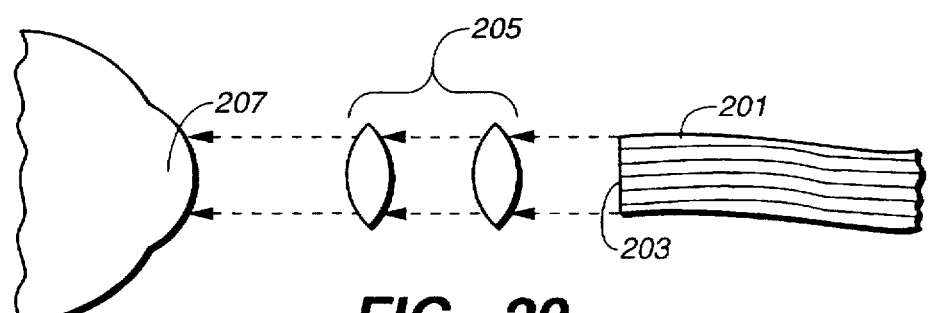
FIG._20

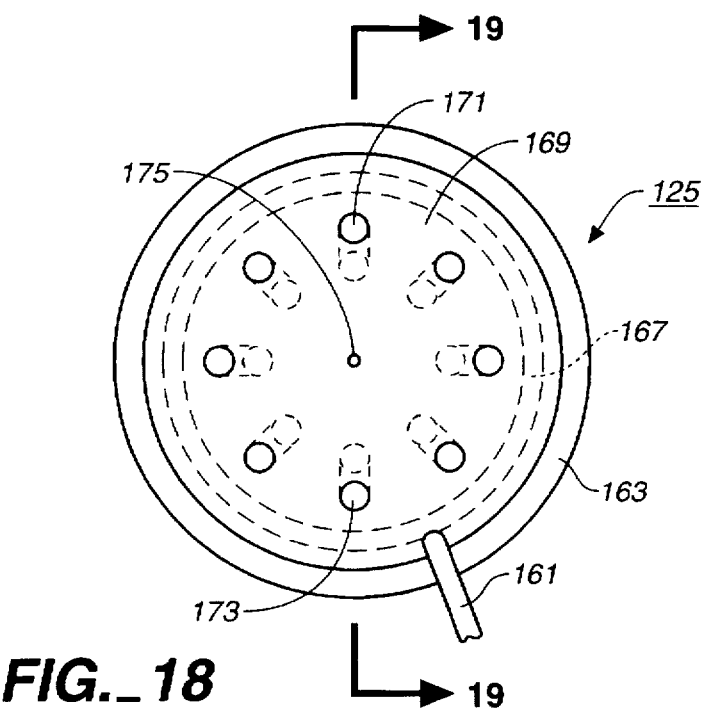
FIG._18
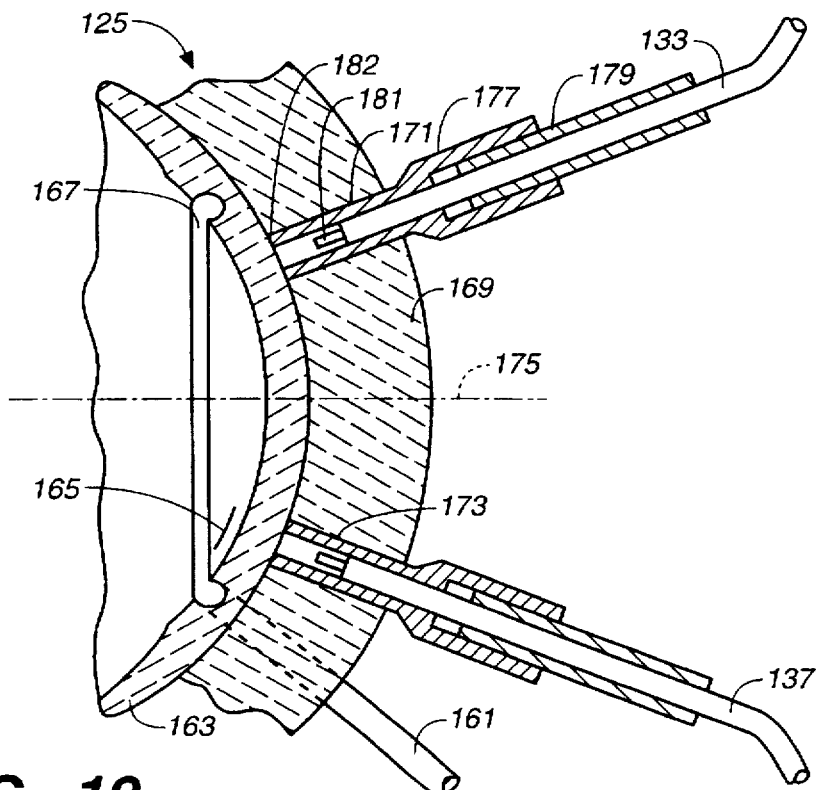
FIG._19

METHOD AND APPARATUS FOR PERFORMING CORNEAL RESHAPING TO CORRECT OCULAR REFRACTIVE ERRORS

CROSS REFERENCE TO RELATED APPLICATIONS

This application is a division of application Ser. No. 08/160,405, filed Dec. 2, 1993, abandoned which in turn is a continuation-in-part of U.S. patent applications Ser. No. 556,886, filed Jul. 23, 1990, now abandoned and Ser. No. 596,060, filed Oct. 11, 1990, now abandoned which are incorporated herein by reference. Applicant claims priority from said applications pursuant to 37 C.F.R. §1.78.

BACKGROUND OF THE INVENTION

This invention relates to a noninvasive ophthalmological method and related apparatus for reshaping the anterior surface of the cornea in order to achieve emmetropia (i.e., normal vision characterized by the absence of ocular refractive error; the emmetropic eye focuses parallel rays of light onto the retina to produce a clear image). It further relates to the use of light to induce thermal changes in the stromal collagen of the cornea to shrink the stromal collagen to produce the desired reshaping of the cornea.

Today there are over 100 million people in the United States alone who wear eyeglasses or contact lenses to correct ocular refractive errors. The most common ocular refractive errors include myopia (nearsightedness), hyperopia (farsightedness), and astigmatism (See FIG. 1). In myopia, the refractive power of the eye is excessive meaning that parallel rays of light are focused in front of the retina producing a blurred image. Myopic vision can be corrected by adding a spherical concave lens of the correct spherical curvature in front of the eye or by flattening the cornea axisymmetrically around the visual axis to reduce its refractive power.

In hyperopia (also termed hypermetropia), the refractive power of the eye is deficient meaning that parallel rays of light are focused behind the retina producing a blurred image. Hyperopic vision can be corrected by adding a spherical convex lens of the correct spherical curvature in front of the eye or by steepening the cornea axisymmetrically around the visual axis to increase its refractive power.

In astigmatism, the refractive power of the eye is unequal in all meridians meaning that parallel rays of light are focused differently along different meridians producing a blurred image. Astigmatic vision can be corrected by adding a non-spherical lens of the correct cylindrical curvatures along various meridians in front of the eye or by flattening and/or steepening the cornea with the correct cylindrical curvatures to compensate for refractive errors along various meridians.

Current widely used devices or methods for correcting ocular refractive errors include eyeglasses, contact lenses and refractive surgery such as radial keratotomy. Eyeglasses and contact lenses may be inconvenient, difficult to wear or impediments in daily activities.

Refractive surgery procedures offer an alternative to eyeglasses and contact lenses but these procedures may be difficult to control in order to achieve accurate refractive corrections. Radial keratotomy is a refractive surgical procedure designed to correct myopia. This technique involves making a series of deep, radial incisions in the cornea with a pattern that resembles the spokes of a bicycle wheel. The incisions themselves do not cross the center of the cornea, the optical zone. The series of symmetrical cuts flatten the cornea.

Significant percentages of patients who have been subjected to radial keratotomy experience overcorrection, undercorrection or induced astigmatism. Radial keratotomy patients may also suffer from side effects and postoperative complications such as fluctuating refraction, glare, reduced night vision, photophobia, endothelial cell loss, and corneal infection. Another postoperative complication of radial keratotomy is permanent weakening of the cornea due to the fact that the technique requires deep incisions that heal quite slowly. Trauma to the eyes may result in the rupture of the incisions leading to catastrophic loss of the cornea in some cases.

Another method of refractive surgery is laser keratomileusis (i.e., carving the cornea by application of laser energy) also termed laser refractive keratectomy or photorefractive keratectomy. This method of refractive surgery is currently being used in clinical trials in man to correct refractive errors. This technique employs the use of a laser that emits ultraviolet light, typically an argon fluoride excimer laser that operates at a wavelength of 193 nanometers. The laser light causes a breakdown of intramolecular bonds resulting in ablation of tissue by photodecomposition. The shape of the cornea is changed by selectively ablating material in the cornea thus "carving" the anterior corneal surface into a new shape. U.S. Pat. No. 4,665,913 discloses one technique of photorefractive keratectomy.

For purposes of this application the "anterior" portion of the corneal stroma should be understood to refer to the first one third of the total depth of the corneal stroma. The stroma is typically 450 microns in total depth and therefore the anterior portion of the stroma should be understood to refer to the anterior-most 150 microns. Preferably the collagen rearrangement resulting from practice of this invention takes place in the anterior-most 100 microns of the stromal collagen and most preferably at a depth of 33–125 microns.

As is the case for other forms of refractive surgery, photorefractive keratectomy may lead to inadequate refractive corrections and to undesirable side effects. Particularly troublesome is the postoperative complication associated with corneal wound repair, a process that tends to "fill in" the ablated cornea volume with a combination of epithelial and stromal tissues. This process in the human cornea is sometimes referred to as a "wound-healing response". There are also concerns about the potential phototoxic effect of ultraviolet light generated by corneal tissue fluorescence and the potential toxic effect of molecular ablation products present in the photoablation plume.

Another method of refractive surgery is intrastromal photorefractive keratoplasty. In this technique a laser beam is focussed inside the corneal stromal tissue to modify tissue either by photoablation or by a change in the tissue's viscoelastic properties. U.S. Pat. No. 4,907,586 discloses one such method. The wavelengths of the laser beams to be used are specified to be 526 nanometers, 1.053 microns, or 2.94 microns. Some of these wavelengths (526 nanometers and 1.053 microns) are transmitted, at least in part, through the cornea possibly causing damage to the retina. If laser induced optical breakdown (i.e., laser induced plasma formation) is used to increase the absorption of these wavelengths, the hot plasma will reradiate light with a broad wavelength distribution that includes phototoxic light in the ultraviolet spectral region. The final wavelength (2.94 microns) specified in U.S. Pat. No. 4,907,586 is absorbed completely in the anterior portion (particularly, the epithelium) of the cornea [G. L. Valderrama, et al., *SPIE Proceedings*, Vol. 1064, 135–145 (1989)] so that it cannot produce intrastromal tissue modification. The alleged intrastromal photorefractive keratoplasty method is unworkable at some wavelengths and undesirable at other wavelengths because there may be severe damage caused to ocular structures.

Thermokeratoplasty is another method that has been used to reshape the cornea. This is done by the application of heat to the cornea. Corneal stromal collagen shrinks when heated to a temperature of 55° to 58° C., without the destruction of the tissue. If the pattern of shrinkage is properly selected the resulting change in the stress field and mechanical properties caused by the shrunken collagen fibers can be used to reshape the cornea.

The original thermokeratoplasty technique used was the application of a heated probe to the cornea leading to conductive heating of the stroma. However, the direct application of a heated probe is uncontrolled and unavoidably destructive. This technique caused thermal destruction of the epithelium as well as Bowman's membrane, the important tissue layer immediately underlying the epithelium. Some patients treated with this technique also showed damage to the deeper corneal stroma and endothelium. Additionally, this technique often involved inadequate refractive correction. Others have attempted the correction of hyperopia by using heated needles to burn a series of craters into the cornea. Recently the hot needles have been replaced with a laser in an effort to produce a more controlled thermal deposition. Severe damage to the corneal tissue still occurs and makes these procedures too undesirable for most ophthalmologists to recommend to their patients.

Another method of thermokeratoplasty involves microwave heating of the corneal stromal collagen Microwave energy can be deposited deeply within the corneal stroma. U.S. Pat. No. 4,881,543 discloses one method and apparatus for heating the central stroma of the cornea with microwave electromagnetic energy to the shrinking temperature of the collagen while circulating a cool fluid over the anterior surface of the cornea. However, microwave thermokeratoplasty procedures do not provide the spatial and temporal resolution and control required to perform accurate corneal reshaping without excessive thermal damage to corneal structures.

Recent thermokeratoplasty techniques are disclosed in the following references: U.S. Pat. No. 4,976,709 issued on Dec. 11, 1990 to Bruce J. Sand entitled "Method For Collagen Treatment"; and Patent Cooperation Treaty Publication Number WO 90/12618 by Kenneth Spears et al. published on Nov. 1, 1990 entitled "Laser Thermal Keratoplasty System". Both of these references disclose and require laser wavelengths and absorption coefficients that result in collagen shrinkage throughout the entire depth of the corneal tissue.

These recent thermokeratoplasty references teach thermokeratoplasty using lasers operating in a frequency range from 1.8 to 2.55 microns with an absorption coefficient range of 15–120 $cm^{-1}$. These devices also use an air coolant applied to the anterior cornea to prevent heat damage to the epithelium and Bowman's membrane. However, at these short wavelengths long irradiation times are required and collagen shrinkage occurs deeper in the stroma. These references do not stress providing adequate cooling for the anterior of the cornea if longer wavelengths are used and do not mask out stray light from areas which do not require treatment to prevent accidental damage to these layers if light should irradiate them. Accidental light irradiation would be even more catastrophic if longer wavelength light were used.

There is still a need for a method of reshaping the cornea that is safe, effective, and dependable. The present invention offers the high spatial/temporal resolution and control necessary for safely using light to reshape the cornea by controlled "heat treatment" of the stromal collagen.

BRIEF DESCRIPTION OF THE DRAWINGS

FIG. 1 is a schematic representation of an emmetropic eye (top) and of eyes having common refractive errors (bottom) including a myopic eye (bottom left) and a hyperopic eye (bottom right). Astigmatism is a refractive error involving combinations of emmetropia, myopia, and/or hyperopia along different ocular meridians.

FIG. 2 is a schematic diagram of the essential components of one embodiment of the apparatus used to perform corneal reshaping to correct ocular refractive errors.

FIG. 2A is a schematic diagram of the essential components of the preferred embodiment of the apparatus used to perform corneal reshaping to correct ocular refractive errors.

FIG. 3 is a schematic cross section of the human eye showing several ocular structures.

FIG. 4 is a schematic representation of corneal microstructure showing important corneal structures.

FIG. 5 shows the distribution of light irradiance I as a function of penetration distance z within corneal tissue for three values of absorption coefficients $\alpha$ at wavelengths $\lambda=1$, 2 and 3. The initial irradiance $I_o$, decreases exponentially to 37% (1/e) of its value at a penetration depth $\delta$ that depends on the incident wavelength of the light. The penetration depth $\delta$ is the inverse of the absorption coefficient $\alpha$ indicated in the figure. Hence, for an absorption coefficient $\alpha$ of 80 $cm^{-1}$, the characteristic penetration depth $\delta$ is 125 μm.

FIG. 6 shows the results of one-dimensional (1D) thermal modelling calculations of temperature distributions as a function of depth of penetration into corneal tissue. Typical depths of microstructural layers of the cornea are indicated for the epithelium (Ep), the Bowman's layer (B), the stroma, Descemet's membrane (D), and the endothelium (En). The calculations use estimated thermal properties (thermal conductivity, thermal diffusivity, and heat capacity) for human corneas together with optical absorption coefficients $\alpha$ pertinent to three laser wavelengths produced by three different laser sources ($CO_2$, HF, and Ho:YAG). All three calculations are for absorbed irradiances of 30 $W/cm^2$ and exposure durations of 80 ms. The desired temperature range (approximately 55° C. to 65° C.) for collagen shrinkage without gross thermal damage is shown within the corneal stroma.

FIG. 7 shows thermal modelling calculations similar to those shown in FIG. 6 except that different temperature distributions are plotted as a function of time (at fixed exposure durations of 1 ms through 10 ms) for application of a hydrogen fluoride chemical laser source (at a predetermined wavelength of approximately $\lambda=2.61$ μm) at a fixed irradiance of 400 $W/cm^2$. Note that the corneal endothelium remains cool in all cases.

FIG. 8 shows thermal modelling calculations similar to those shown in FIG. 6 except that the temperature distribution that peaks on the anterior surface (z=0) of the cornea is for application of a hydrogen fluoride (HF) chemical laser source (at a predetermined wavelength of approximately $\lambda=2.61$ μm) at a fixed irradiance of 30 $W/cm^2$ and a fixed time of 80 ms. The temperature distribution that peaks within the anterior portion of the stroma is calculated for the same laser wavelength but includes the effects of a heat sink/coupler in thermal contact with the anterior surface of the cornea. In this case, the HF chemical laser source is applied for a fixed irradiance of 100 W/cm² and a fixed time of 100 ms.

FIG. 9 is a schematic representation of different patterns of treatment on the anterior surface of the cornea The annulus has a radius R and a width Δ and is drawn using a laser spot that is slewed at an angular velocity Ω.

FIG. 10 shows experimental corneal curvature (dioptric, or refractive, power) measurements for both untreated (control) and treated eyes of the example rabbit (Ignatieff) at different observation times.

FIG. 11 is a schematic representation of the fiber optic array used in the apparatus of the preferred embodiment of the invention.

FIG. 12 is a schematic representation of one strand of optical fiber used in the fiber optic array used in the apparatus of the preferred embodiment of the invention.

FIG. 13 is a schematic cross-sectional view of a device for coupling to the eye while reshaping its cornea.

FIG. 14 is a schematic assembly of the platform, articulated arm, coupler device and related equipment used to perform cornea reshaping.

FIG. 15 shows an alternative embodiment of a system for corneal reshaping, including a bundle of optical fibers terminating in the coupler of FIG. 13.

FIG. 16 is a view of the eye contacting surface of the coupler of FIG. 15, as viewed from a direction of the arrows 16—16 of FIG. 15.

FIG. 17 shows yet another embodiment of a system for corneal reshaping that uses only a few optical fibers that are detachably connected to a corneal coupler, an inventory of differently shaped couplers being provided for various specific corneal reshaping procedures and patients.

FIG. 18 is a view of the corneal coupler of FIG. 17, as viewed from position 18—18 of FIG. 17.

FIG. 19 is a cross-sectional view of the corneal coupler of FIGS. 17 and 18, taken at section 19—19 of FIG. 18.

FIG. 20 illustrates an alternative embodiment using a bundle of optical fibers to define the corneal exposure pattern, which pattern is then imaged onto the anterior surface of the cornea.

SUMMARY OF THE INVENTION

This invention provides an improved method for reshaping the cornea to correct ocular refractive errors such as myopia, hyperopia and astigmatism. This invention also provides an improved method for delivery of the correct dose of photothermal radiation to the corneal tissue region required to cause collagen shrinkage without photodecomposition and to produce accurate control of the corneal reshaping process. This process is known as photothermokeratoplasty. This invention further provides light source parameters to assure safe and effective corneal reshaping. One embodiment of this invention provides for a heat sink at the anterior surface of the cornea to prevent damage to the epithelium and Bowman's membrane. Another embodiment provides for a solid heat sink to act as a template for the predetermined physical changes to the curvature of the corneal tissue. Still another embodiment provides a fibre optic array to control the light energy applied to the cornea.

This invention provides a noninvasive method and apparatus for reshaping the corneal tissue by exposing the cornea to a functionally effective amount of light energy in a spatially localized pattern. The light energy is applied at one or more predetermined wavelengths between 1.87–2.08 or 2.55–2.7 microns, irradiance levels and time durations to thermally induce predetermined, physical changes to the curvature of the cornea. This invention also provides a method of inducing the above changes without inducing a wound-healing response in the stroma sufficient to significantly change the corneal curvature from its predetermined value and without damaging the viability of the corneal endothelium or the anterior surface of the corneal tissue. The invention further provides an embodiment wherein the physical changes are induced by more than one exposure to a functionally effective amount of light energy. Depending on the severity of the treatment, it is possible to avoid exposure of the central optical zone during treatment. However, the decision as to whether or not to include the central optical zone in the spatial pattern of treatment is within the discretion of the patient.

It further provides a method wherein one or more predetermined wavelengths, irradiance levels and time durations are functionally effective to produce a predetermined change in only the anterior portion of the stroma. The preferred depth of penetration of light into the cornea is about 33 microns to about 125 microns. The preferred irradiance level of light energy is at a level where the absorption is substantially linear, and most preferably where the absorption coefficient is 30 cm$^{-1}$ to 100 cm$^{-1}$ at the 1.87–2.08 micron wavelength range or 100 cm$^{-1}$ to 300 cm$^{-1}$ at the 2.55–2.7 micron wavelength range. The preferred time or duration of exposure is less than about one second in each portion of the pattern of application. The preferred light source is an erbium light source with the preferred wavelengths generated from the light source being about 2.55 to 2.7 microns. The light source may be either a coherent light source or a non-coherent light source. The most preferred embodiment is a non-coherent erbium light source. Other preferred light sources include holmium, thulium, and uranium based light sources, both coherent and non-coherent, and combinations thereof.

Experimentation has shown that it is essential that the stromal collagen temperature be preferably heated to about 55° C. to 65° C. during the thermal modification portion of the method although treatments in a temperature range of 55° C. to 75° C. have been functionally satisfactory. Below about 55° C. there is no apparent physical effect and above 75° C. there is permanent damage although in the 65° C. to 75° C. range permanent damage can be avoided by limiting the exposure time to the temperature to very short "flash" exposures. In the preferred embodiment, the temperature of the endothelium does not exceed 55° C. during the application of the light energy. The invention further optionally provides for a transparent heat sink to prevent damage to the anterior surface of the corneal tissue while exposing the stromal collagen portion of corneal tissue to the light energy. The stromal collagen is heated to a temperature of about 55° C. to about 75° C. . The invention further provides for the optional use of a coupling device during the application of light energy to couple light energy onto the cornea with precise control of position and initial temperature while providing protective functions for corneal structures that are not being reshaped. The coupling device further provides a mold or template for the predetermined anterior corneal curvature.

For purposes of this invention it is important to understand the interrelationship of light energy, stromal temperature, heat energy, heat sink, physiological rearrangement of stromal collagen, and time. Functionally, the purpose of this invention is to cause a predetermined, beneficial rearrangement of the anterior stromal collagen without initiating a wound healing response. In order to accomplish the desired rearrangement a specific quantum of light energy is applied to the anterior stroma of the cornea. It is intended that enough light energy be applied to cause the desired physiological change to the anterior stroma without at the same time initiating a wound-healing response in the cornea and without damaging the heat sensitive endothelium, epithelium or Bowman's membrane. Experimentation has verified that a safe temperature range to accomplish the intended rearrangement is 55° C. to 65° C. However, stromal temperatures up to 75° C. can be tolerated, and will result in the desired physiological rearrangement, if the exposure to temperatures from 65° C. to 75° C. is maintained at "flash" duration. If the stromal temperature is maintained at 65° C.–75° C. for an extended time period, e.g., one second or more, then although the desired physiological rearrangement will occur, the undesirable wound-healing response will also be initiated.

It is likewise important for an understanding of the physiological effect of this invention to understand the desired depth of penetration of the changes in the cornea. As has been previously stated absorption coefficients of 30 cm$^{-1}$ to 100 cm$^{-1}$ and 100 cm$^{-1}$ to 300 cm$^{-1}$ are preferred in the practice of this invention. This corresponds to a cornea depth of 33–333 microns which would indicate that a physiological change was taking place outside of the stroma at the smallest penetration depths (e.g. 33–60 microns). However, the use of a heat sink on the exterior surface of the cornea permits cooling of the epithelium and Bowman's layer so that heat transfer modifies the depth of penetration of physiological changes. It should be understood that "peak" temperatures would occur only in the stroma with lesser temperature changes occurring outside the stroma being insufficient to cause either a wound healing response or physiological change.

DETAILED DESCRIPTION OF THE INVENTION

It is the purpose of the current invention to provide a noninvasive method for performing accurate, controlled reshaping of the anterior surface of the cornea in order to correct ocular refractive errors. The invention uses a light source emitting a wavelength or wavelengths with correct optical penetration depths to induce thermal changes in the corneal, stromal collagen without damaging the viability of the corneal endothelium or the anterior surface of the corneal tissue and without causing a sufficient wound-healing response to lead to long-term or permanent corneal reshaping. The light source is coupled with light delivery and control means for producing the required radiant exposure time and geometric pattern in order to achieve the desired change in the shape of the cornea (sometimes referred to as a physiological rearrangement of the stromal collagen). Anterior corneal surface cooling by a transparent heat sink may be used to prevent damage to the endothelium and to Bowman's layer and to insure desired temperature at preferred depths of the stroma. Although the method is described herein as being performed only one time, repeated applications of the method may be desirable or necessary and are included within the scope of the invention.

The curvature of the cornea in part controls the refraction of the light received by the lens of the eye. Ocular refractive errors of the eye can be corrected by changing the shape of the cornea. FIG. 3 identifies the various portions of the human eye schematically. As is apparent from the representation of the human eye in FIG. 3, only a small portion of the cornea is used for actual vision. This portion of the cornea is typically referred to as the central optical zone or central visual zone. The typical central optical zone is 4 millimeters in diameter. Referring now to FIG. 4, a cross-section of the cornea is shown together with its various layers. As represented schematically, the epithelium is several layers thick and approximately 40 microns in depth. Bowman's membrane is thinner, approximately 15 microns thick, and the stroma layer is the thickest structure, typically about 450 microns thick. For purposes of this application the anterior portion of the stroma is the anterior one third of the stroma or approximately the first 150 microns of the stromal tissue.

The stroma is composed of various internal layers with the arrangement of the layers being the least organized in the anterior section of the stroma. For purposes of this application, corneal tissue shall refer to the entire corneal structure as shown in FIGS. 3 and 4. The anterior portion of the stroma (as opposed to cornea) is that portion that demonstrates a more random lamellar structure and typically corresponds to the anterior-most 150 microns. The organic matter within the corneal stroma is primarily made up of Type I collagen. The Type I collagen of the cornea, before heat treatment, is composed of triple helix strands of polypeptides. The polypeptides are held together by hydrogen bonds between the polypeptide strands. On heating the collagen reforms so that the overall length is decreased. This thermal modification phenomenon is called collagen shrinkage. One object of this invention is to allow for ocular changes in the stroma without harming the viability of the other layers. Although some damage is inherent in this method, retaining viability means that the eye continues to function optically and that the cellular layers continue to live and regenerate.

Heating the collagen of the stroma to a temperature of at least 55° to 58° C. and up to a maximum of about 75° C. causes the collagen to shrink thereby changing the shape of the cornea. This heating process can be effectuated by directing light energy onto the cornea to cause absorption of energy to heat the stromal collagen to the desired temperature. This is done by providing a light source that radiates light energy that is characteristically deposited within a specified depth of the corneal tissue. Light energy as used in this application is not limited to the visible spectrum. The selection and control of the source of light energy that induces the thermal changes to the cornea is critical. The variables used to select the appropriate amount and type of light energy are wavelength, irradiance level, and time (duration). It is essential that these three variables be selected so that the amount of light is functionally effective to produce a predetermined change in the anterior portion only of the stroma. The light source can be either a laser (coherent light) or a non-laser (non-coherent light) light source providing it emits radiation of the appropriate wavelengths to be absorbed within the anterior portion of the stroma without penetrating deeply into the eye in a manner that can damage the endothelium of the cornea or other structures of the eye. The light radiation must also be of a type that can be directed onto the cornea and controlled to produce the appropriate thermal changes.

It should be understood that the term wavelength includes wavelengths of slightly greater and slightly smaller size and is often described for purposes of this application as "one or more wavelengths." It has been found in the current invention that the optimum wavelength ranges are about 1.87 microns to about 2.08 microns and about 2.55 microns to about 2.7 microns. Light within this range of wavelengths is absorbed primarily in the anterior portion of the stroma (See FIG. 5). In general, this invention includes light having wavelengths that are absorbed within a penetration depth of 33 to 125 microns within the cornea. Since human corneas are typically 500 microns or more in thickness the initial absorption of light energy at these wavelengths does not heat the corneal endothelium significantly thus preventing damage to this vulnerable structure. By controlling the duration and irradiance level of light emitted at these wavelengths, substantial thermal conduction of the absorbed light energy can be prevented so that the conducted heat does not damage the corneal endothelium.

The selection and control of the source of light energy that induces the thermal changes to the cornea is critical. The variables used to select the appropriate amount and type of light energy are wavelength, irradiance level, and time (duration). It is essential that these three variables be selected so that the amount of light is functionally effective to produce a predetermined change in the anterior portion only of the stroma without at the same time causing a wound healing response.

Light sources should be used which produce wavelengths for which the absorption coefficient of corneal tissue is in the range of 30 $cm^{-1}$–100 $cm^{-1}$ (wavelengths of 1.87–2.08 microns) and 100 $cm^{-1}$–300 $cm^{-1}$ (wavelengths of 2.55–2.7 microns), corresponding to optical penetration depths in the range 33.3–333 microns. Light sources producing absorption coefficients between 30 $cm^{-1}$–100 $cm^{-1}$ or 100 $cm^{-1}$–300 $cm^{-1}$ have wavelengths in the range of 1.87–2.08 µm or 2.55–2.70 µm, respectively, for the ordinary physiological temperatures of the cornea. At elevated temperatures, however, there may be changes in absorption coefficients and resulting changes in depth of penetration of the cornea Therefore, it should be understood that the absorption coefficients and related penetration depths are for temperatures at or near physiologically typical temperatures.

One preferred light source is a hydrogen fluoride light source. The most preferred light sources are holmium, erbium, thulium and uranium based non-coherent light sources, or combinations thereof. The light source is tuned to produce only those wavelengths of radiation that are characteristically absorbed in the first 33 to 125 microns of the cornea. The wavelengths chosen for use in this invention fall within the range of approximately 1.87–2.08 microns and 2.55–2.7 microns. An example of one light source that can be utilized in the current invention is a modified Helios hydrogen fluoride mini-laser (Helios Inc., Longmont, Colo.). This modified laser system uses special resonator optics that are designed to allow laser action on certain hydrogen fluoride wavelengths while suppressing all other wavelengths.

To achieve treatment of only the anterior portion of the stromal collagen, either an incoherent light source or laser light source, either with a wavelength of 1.87–2.08 µm or 2.55–2.70 µm, can be used. Two possible materials to form lasers in the acceptable wavelength range are listed as follows:

(1) KCl:Li $F_A(II)$ color center crystals can be used to fabricate tunable color center lasers in the wavelength range 2.5–2.9 µm. At a low temperature, these lasers have very high fluorescence quantum yields of conversion from visible light to infrared light. Conversion from visible light to infrared light is required so that temperature of the stroma is increased. FIG. 5 shows the measured fluorescence and relative laser efficiency taken from L. F. Mollenauer, "Broadly Tunable Lasers Using Color Centers", in S. Haroche, et al., *Laser Spectroscopy* (Springer-Verlag, New York, 1975) pp. 227–238. The solid curve of FIG. 5 is the luminescence and dots show the 1/P threshold.

(2) Erbium-doped crystals, such as $ER^{3+}$:YAG or trivalent erbium ions doped in yttrium aluminum garnet, are used to make fixed frequency solid state lasers in the wavelength range 2.7–3.0 µm. These lasers also have high fluorescence quantum yields of conversion from visible light to infrared light. Another dopant such as chromium ions in combinations such as Cr:Er:YAG and Cr:Er:YSGG permits broadband pumping to achieve additional power from erbium ions by energy transfer from chromium ions. Besides the above two listed light source materials, other materials may be used to form efficient light sources in the wavelength region 2.55–2.7 µm.

FIG. 6 is a graphic representation of temperature in the various layers of the cornea during the application of light energy using various laser light sources at a constant time and irradiance level. Note that the HF laser (at a predetermined and selected wavelength of approximately 2.61 µm for the calculation shown) heats the anterior portion of the stroma to the correct temperature while keeping the endothelium cool and the epithelium at a high, but moderate, temperature. Temperatures at the surface of the cornea are in a range easily controlled by a heat sink. Under the same conditions, the $CO_2$ laser generates very high temperatures within the epithelium and within Bowman's membrane leading to extensive thermal damage to these structures. The temperature then very quickly drops below the effective temperature of 55° C. because penetration into the cornea is so poor. The primary mechanism of energy deposition is thermal conduction of heat into the tissue interior from the epithelium where it is absorbed. Again under the same conditions, the Ho:YAG laser does not generate sufficient heating of the anterior portion of the stroma to produce collagen shrinkage and corneal reshaping; the Ho:YAG laser does, however, heat the endothelium to nearly the same temperature as that obtained in the anterior portion of the stroma since the wavelength (2.1 µm) of the Ho:YAG laser is much more readily transmitted through corneal tissue.

The light source is combined with a means of directing and controlling the light beam from the light source accurately onto corneal surfaces. This will generally include an optical delivery system consisting of beam directing or focusing optics together with an optical shutter or related materials and devices. The optical delivery system allows control of the delivery parameters such as geometry and dose to produce the desired predetermined reshaping of the cornea. It also allows the control of the irradiance level and duration of the light energy directed upon the eye necessary to heat the collagen in the cornea to the point where it will shrink but not be destroyed and to prevent conduction of the thermal energy that could damage the endothelium.

The preferred duration of exposure of the cornea to or time for application of the light energy is less than about 1 second. Most preferably the time exposure is from about 10 milliseconds to about 100 milliseconds, with the most preferred duration being approximately 10 to 50 milliseconds. The light energy is actually applied in an intermittent or pulse form with each pulse being less than 1 second. The level of irradiance is typically selected to be a level wherein absorption is substantially linear. In the most preferred embodiments of this invention, the irradiance level is less than $1\times10^8$ W/$cm^2$ and preferably less than $1\times10^3$ W/$cm^2$ and most preferably wherein the absorption coefficient is within ranges of about 30 cm$^{-1}$–100 cm$^{-1}$ or 100 cm$^{-1}$ to 300$^{-1}$. The variables of wavelength, duration and irradiance are highly interdependent. These variables must be interrelated in a way that a functional amount of light is delivered to the cornea to make the desired predetermined physical changes in the curvature of the cornea without eliciting a wound healing response. A preferred interrelationship of variables includes wavelengths of 1.87 to 2.08 microns or 2.55 to 2.7 microns, a duration of less than 1 second and an irradiance level wherein the absorption coefficient is 30 cm$^{-1}$ –100 cm$^{-1}$ or 100 cm$^{-1}$ to 300 cm$^{-1}$. FIG. 7 shows graphically the effect of exposure time at a fixed wavelength and irradiance level.

Various geometric patterns and temporal periods of radiation produce corrections of different types and magnitude of ocular refractive errors. Referring now to FIG. 9, various geometric patterns and spatial orientations of treatment zones are shown that provide the desired corrective effect. Tangential lines, radial lines, annular rings, and combinations have been shown to be useful in obtaining corrective measures with this invention. In all cases the method results in patterns of shrinkage.

It is critical that at no time during or after application of the functionally effective dose of light in association with the method of this invention is a substantial woundhealing response initiated in the cornea and specifically, in the stromal tissue of the cornea In this connection, a substantial wound-healing response is one that causes stromal collagen synthesis and regrowth that produces a change in curvature of the anterior surface of the cornea. The corneal wound-healing response in man is complex and not perfectly understood [R. W. Beuerman, C. E. Crosson, and H. E. Kaufman (editors), *Healing Processes in the Cornea* (Gulf Publishing Co., Houston, Tex., 1989)].

Following a substantial wound to the stromal tissue, a sequence of processes occurs that result in the synthesis of new collagen that is initially present in the form of disorganized fibers of nonuniform diameters and irregular orientations. These new collagen fibers degrade corneal transparency since they scatter light. Over a period of several months, the new collagen fibers may be transformed, at least in part, into new stromal lamellae that have more organized structures that transmit light properly without scattering. As these new stromal lamellae are formed, the dimensions and mechanical properties of the stromal tissue change, thereby causing changes in anterior corneal shape. In the present invention, a substantial wound-healing response is avoided by careful control of the nature and extent of stromal collagen alternation. Therefore, the results of the corneal reshaping produced by application of a functionally effective dose of light are predictable and controllable and are not subject to long-term modification due to a substantial wound-healing response. Alternate procedures such as excimer laser photorefractive keratectomy suffer from instability of refractive correction due to longterm stromal regrowth and corneal reshaping.

In one embodiment of the invention the output beam of radiation from a hydrogen fluoride chemical laser is directed by a series of beam steering mirrors onto an X-Y scanner. The scanner is driven by computer controlled electronics to produce a swept beam that is directed onto a focusing lens that produces a specified beam diameter on the front surface of the cornea. The focused beam is applied over the front surface of the cornea with a specified application rate and geometric pattern. A computer controlled optical shutter is used to control the temporal duration of application of the slewed beam which may be continuous or interrupted during laser irradiation of the cornea. Many variations and combinations of optical delivery systems are available and are known to those skilled in the art. Any optical delivery system which will provide the precision necessary to practice the current method will suffice.

A means to measure the curvature of the cornea before, during and after the cornea reshaping process is utilized. Any keratometric device, such as a video keratometer, can be used to produce accurate corneal topographic maps of the cornea. The corneal topographic maps, together with refractive measurements of the eye, are used to establish the geometry and dose of light energy required to produce correction of ocular refractive errors. After the application of light energy, keratometric measurements are performed to produce corneal topographic maps that verify that the desired correction has been obtained. Keratometric measurements may also be made during the cornea reshaping process as multiple applications of light energy may be needed to reach the correct "end point" (an emmetropic eye). Examples of keratometers which may be used include the EyeSys Corneal Analysis system, and the PKS-1000 photokeratoscope (Sun Contact Lens Co. Ltd., Palo Alto, Calif.). A preferred keratometer will provide digitized output from which a visual display is producible to show the cross-section al profile of the anterior surface curvature of the cornea.

Also provided by this invention is a means for cooling the anterior surface (understood to be the epithelium and Bowman's membrane) of the cornea during the reshaping process to prevent damage to the corneal epithelium and to Bowman's membrane. This is done by providing a transparent heat sink. It will be obvious to those skilled in the art that the heat sink must be effective enough to prevent damage to the epithelium and Bowman's membrane but not so efficient as to prevent the necessary amount of collagen shrinkage to provide the desired ocular refractive correction. Heat sinks that are suitable for anterior surface cooling include transparent fluids, either gas or liquid, which can be circulated over the anterior corneal surface to provide cooling by forced convection. Any transparent fluid may be used which will not harm the eye and which will serve to adequately cool the cornea. A transparent solid heat sink, such as a hard contact lens which has sufficient thermal conductivity, thermal diffusivity, and heat capacity to provide cooling by conduction may also be used.

As shown in FIG. 9, it is important that the light energy be applied in a spatially localized pattern. The localized pattern includes any number of radial lines, transverse lines, a pattern of spots or annular rings depending upon the desired type and degree of correction. To assist in such correction, a specifically designed coupler, often utilized as a heat sink, may also be used. Such a coupler can be made of any of a number of materials but most preferably of Infrasil quartz or sapphire. With such materials, a coupler can be created which cools the anterior surfaces of the cornea to prevent inappropriate heating and damage. The coupler can also be used as a mask to prevent accidental exposure of the non-treated portions of the cornea to any light energy and as a restraint to prevent movement of the eye. Additionally, thermocouples can be attached to the coupler to monitor temperatures and the coupler can be mounted in a thermostatically controlled chamber to provide reproducible pre-operative corneal temperature. Finally the coupler can be used to accurately position the pattern of localized light application.

In one embodiment of the current invention, the transparent solid heat sink or coupler is designed and constructed with the correct curvature in contact with the anterior surface of the cornea to provide a template or mold for the control of the cornea reshaping process. In this embodiment the correct "end point" for cornea reshaping is produced by simultaneously shrinking, swelling, and molding the corneal stromal collagen into the correct final shape. Stromal collagen is a "thermoplastic" material that can be thermally formed into new shapes when it is subjected to mechanical forces. During thermal processing at the collagen shrinkage temperature, collagen shrinks along the main fiber axis direction to a new length that is determined in part by the tension acting along the fiber direction [J. C. Allain et al., *Connective Tissue Research*, 7, 127–133 (1980)]. Collagen swells transverse to the main fiber axis direction.

At elevated temperature (i.e., at the corneal shrinkage temperature), collagen is much less rigid due to the loss of weak bonds (termed hydrogen bonds) that hold collagen molecules in a precise structural pattern (a triple helix) at physiological temperature. Hence, at the collagen shrinkage temperature, stromal collagen is much more plastic and is capable of being molded into a new shape. Once formed into a new shape at the collagen shrinkage temperature, the stromal collagen may then be cooled to physiological temperature. At physiological temperature, new hydrogen bonds form and these tend to preserve the stromal collagen in its new shape. Sapphire and Infrasil quartz (a type of quartz that has high transparency to the preferred wavelengths of functionally effective light) are examples of appropriate solid materials that are transparent to the wavelengths of functionally effective light, that have good thermal properties to serve as a heat sink, and that have mechanical rigidity to act as a template or mold for the reshaping of the anterior surface of the cornea.

FIG. 8 is a graphic representation of temperature in the various layers of the cornea using a hydrogen fluoride laser. The graph shows the effectiveness of using a heat sink or coupler. With the extra control provided by the coupler, light energy of a higher irradiance level with a longer exposure time resulted in harmless temperatures in the epithelium and Bowman's membrane while allowing functionally effective temperatures within the anterior portion of the stroma.

A typical laser apparatus for practicing this invention is described below. The light source, a hydrogen fluoride chemical laser or erbium-based laser, is installed either in the patient treatment room or in a remote location. The light source beam either is propagated through an optical path in air or is coupled into a fiber optic cable. The propagated or coupled beam is then directed onto beam steering, scanning, and focussing optics. An optical shutter is also incorporated within the beam train to provide the correct exposure duration. The beam delivery system includes the scanning system that controls the movement of the laser beam on the predetermined and preselected portion of the patient's cornea.

Additionally, the shutter and scanning system are computer controlled to synchronize their actions and to obtain accurate delivery of the functionally effective light beam onto the patient's cornea. The final delivery optics of the optical delivery system are mounted securely on the patient treatment table. These optics have XYZ coordinate translation adjustments and ΘΦ angular adjustments to permit the beam to be aligned and positioned accurately with respect to the eye that is to be treated.

A beamsplitter is used to sample a small portion (typically, a few percent) of the final output beam that is to be directed onto the patient's eye. This small portion of the beam is directed to beam diagnostic instrumentation to measure laser beam parameters such as power, spot size, and irradiance distribution. The patient sits upright at a slit lamp that includes a chin rest, a head mount for accurate positioning, and an accessory mount that contains the coupler to provide protection to the anterior surface of the cornea, shape the cornea by action of a template surface, mask the surface regions of the cornea that are not to be treated, and thermostatically control the initial corneal temperature. The patient is looking horizontally forward into the coupler and a fixation light source. The treatment light beam is directed horizontally forward through the coupler onto the patient's cornea that is to be treated.

The physician who performs the treatment uses a slit lamp microscope, together with a visible tracer light beam (from a low energy visible light source) that is collinear with the treatment beam, in order to verify the proper positioning of the treatment beam.

One embodiment of the apparatus of this invention is illustrated schematically by the flow chart in FIG. 2 while a more preferred embodiment is shown in FIG. 2A. This flow chart is intended to show a control means utilized by the physician as the focal point for controlling all variables and light emission devices. The control means is connected to the laser system, the beam delivery system, the scanning system and the keratometer. A light source (in the figure, a laser system) is used to produce functionally effective light. The beam of light is delivered and scanned to produce the correct pattern and dose of functionally effective light on the anterior surface of the cornea. A coupling means is used to provide a heat sink for protection of the anterior surface of the cornea, a template for reshaping the anterior surface of the cornea, a thermostat for accurate and reproducible temperature control prior to laser treatment, a mask for protection of regions of the anterior surface of the cornea that are not intended to be treated, and a positioner/restrainer for accurate positioning of the light source beam on the anterior surface of the cornea and for restriction of eye movement during the treatment. A keratometer is used to perform corneal topography measurements before, during, and after the procedure.

A control means is used to provide predetermined values of pattern and dose of the laser beam on the anterior surface of the cornea. It is suggested that the control means have all the controls necessary for the surgeon to have complete control of the operation including suitable displays of the operation variables showing what has been preselected and what is actually delivered. For example, the pattern of the laser beam should be preselected and be capable of being varied by the surgeon. The pulse duration, the number of pulses to be delivered, the number of pulses actually delivered to a particular location on the eye and the power of each pulse should also be controlled. The control means may be a suitable computer with a terminal at the surgeon's location allowing display of all elements of the operation which may be of interest to the surgeon.

A typical non-coherent light energy source and apparatus for practicing the method of this invention is shown in FIG. 2A. The essential components of the system are labelled and identified in FIG. 2A. The light source, a fluorescer that is activated by a diode laser, is installed in a patient treatment room. Activation light from a diode laser is coupled into optical fibers that are mounted in a fiber optic array. Each proximal tip of each optical fiber is positioned separately by a translation stage driven by a computer-controlled position controller so that the diode laser beam is properly focused into each proximal tip. The diode laser is driven by a pulsed power supply that is also computer-controlled. With this system, a controlled and pre-specified amount of diode laser light is directed into each optical fiber for a pre-determined time.

The fiber optic array guides diode laser light pulses to the array of fluorescer elements schematically shown in FIG. 11. In this figure each dark element has been activated to form an annulus of fluorescers that are located at the distal ends of optical fibers through which diode laser light has been channeled. With this system, a predetermined pattern of individual fluorescer elements is activated in a pre-determined sequence for pre-determined periods of time.

FIG. 12 shows a detail of one optical fiber/fluorescer assembly. The optical fiber is bonded to the fluorescer and efficiently transmits diode laser light near a wavelength of 785 nanometers into the fluorescer. Fluorescence light of functionally effective wavelengths radiates from the fluorescer, through an optical filter (to restrict fluorescence to a predetermined wavelength band and to remove any remaining diode laser light), and through a window/coupler into the corneal tissue to be treated. A dichroic optical coating is used at the optical fiber/fluorescer interface to transmit diode laser light and to reflect fluorescer light. The fluorescer has a totally reflective optical coating on its sides and also has a dichroic optical coating on its exit face to transmit fluorescer light while reflecting diode laser light. All of these optical coatings improve the efficiency of projecting fluorescer light into the corneal tissue to be treated.

Referring to FIG. 13, the coupler device is shown in schematic cross section. The primary components of the coupling device 10 are transparent body 11, suction ring 20, corneal engaging surface 30 and an optional mask 40. The cornea itself is identified by the number 50 and the central optic portion of the cornea by the number 60. It is sometimes desirable that the central optic portion 60 of the cornea 50 not be illuminated, so the mask 40 can be employed in such incidences to block incident radiation 70 in this area. The incident light energy 70 is emitted from an appropriate energy source, i.e., a hydrogen fluoride, thulium or holmium doped laser.

The corneal engaging surface 30 of the coupler 10 acts to interface between the coupler device 10 and the cornea 50. The coupler device 10 is maintained in position by suction ring 20 which is sized to encompass a substantial portion of the human cornea. It is anticipated that a film of tears or ophthalmic solution may be found between the coupler device 10 and cornea 50. The coupler device 10 is removably attached to the anterior surface of the cornea.

The central portion 11 of the coupler 10 is made from a transparent material such as Infrasil quartz (a purified form of quartz that is highly transparent to radiation at about 2 microns in wavelength), calcium fluoride, sapphire, diamond, or a fluoro-polymer material such as that available from Fresnel Technologies of Fort Worth, Tex., as "Poly IR5". Other materials that satisfy the functional characteristics of providing a heat sink, template, thermostat, positioner, restrainer and mask can likewise be used. The coupler is used by grasping the suction ring 20 on its outermost edges 21 and pressing the device onto the corneal surface. In this fashion the suction ring acts as both a means for restraining movement of the eye and a means for immobilizing the eye. Since the body 11 is transparent, the operator has the benefit of viewing the eye through the body 11 in order to properly position the coupler 10 with the pupil of the eye 50 substantially centered within the ring 20. In one implementation, the coupler 10 is removably mounted in a stable platform 80 (see FIG. 14) to insure that the eye, coupler and light source are maintained in coaxial alignment for the duration of irradiance. The stable platform includes an articulate arm 81.

In FIG. 14, a schematic representation of the stage assembly 80 with the coupler 10 in place over the eye 50 is shown. Optical connections are conveniently made as part of a beam delivery system (also referred to as light energy source) 70 by fiber optic cable. A control panel is actuated and used by the operator to control a display so that appropriate surgical modification can be made to the eye.

An operator has access to the means for determining the change of shape of the cornea of the eye, in the preferred embodiment a surgical keratometer, and also to the means for viewing the cornea 50 of the patient's eye, in the preferred embodiment an ophthalmic surgical microscope.

The coupler 10 is adapted for use in combination with a noninvasive ophthalmological method for reshaping the anterior surface of the cornea in order to achieve emmetropia (normal vision). The coupler 10 is positioned over the eye 64 during the reshaping procedure. The coupler 10 is made of a material that is substantially transparent to the light energy being used to reshape the cornea 50. The functions of the coupler 10 include acting as one or more of: (1) a heat sink and thermostat; (2) a template for the cornea; (3) a positioner and restrainer for the eye; and (4) a mask during the reshaping procedure.

The coupler 10 consists of two major functional parts. The first part is an annular suction ring 20 shown in FIG. 13. The purpose of the annular suction ring 20 is to attach the coupler to the eye by use of a vacuum. A vacuum of approximately 10 mm. of mercury (Hg) is used. The functions of positioning and restraining the eye 64 are accomplished by attaching the coupler 10 to the eye 64. These functions are achieved because the couplers 10 can be positioned and maintained in place during the procedure; therefore by being attached to the eye 64, the eye 64 will also be positioned and restrained.

The coupler 10 has its substantially transparent center portion 11 with a radially curved surface 30 which approximates the desired emmetropic shape of the anterior portion of the cornea. (FIG. 13) This part of the coupler performs the functions of acting as a heat sink and thermostat, and, optionally, a template for the cornea and a mask during the reshaping procedure.

The heat sink and thermostat function is desired as a means of maintaining the epithelium and epithelial basement membrane at a sufficiently cool temperature during treatment in order to prevent clinically significant damage, particularly to the important basement membrane layer. The epithelial basement membrane controls the attachment of epithelial cells to the underlying Bowman's layer of the cornea. It must be protected during the heating of the stroma.

The corneal engaging surface 30 of the coupler 10 (FIG. 13) has a radius of curvature which approximates the desired emmetropic shape of the cornea to be formed by the reshaping procedure. The corneal engaging surface 30 actually rides on a thin tear film or ophthalmic solution on the surface of the cornea. A thin ophthalmic solution film can be used in conjunction with the coupler to prevent damage to the epithelium.

The masking function of the coupler is optionally performed by blocking all light energy from impacting on any portion of the cornea desired to be protected from any effect of the radiation, such as the central optic zone of the eye. This prevents inadvertent reshaping of any portion of the cornea that is not desired to be treated.

The reshaping procedure uses a light source 70 emitting a wavelength or wavelengths with correct optical penetration depths to induce thermal changes in the corneal stromal collagen without damaging the viability of the corneal endothelium or the anterior surface of the corneal tissue and without causing a sufficient wound-healing response to lead to long-term corneal reshaping. The light source is coupled with a light delivery and control means for producing the required radiant exposure time and geometric pattern in order to achieve the desired change in the shape of the cornea. Anterior corneal surface cooling by the coupler is used to prevent damage to the epithelium and epithelial basement membrane.

Another system for delivering a controlled infra-red electromagnetic radiation pattern is described in copending U.S. patent application Ser. No. 07/923,813, filed Aug. 3, 1992, by David R. Hennings and Ralph W. Olenick, the disclosure of which is expressly incorporated herein by this reference. The system there described projects a symmetrical octagonal pattern of spots onto the outside of the cornea, the spots being arranged with equal spacing around a circle having a controllable diameter. Each of the eight spots is individually shuttered so that fewer than all of the spots may be selected for any particular treatment. Of course, some number of symmetrically spaced radiation spots other that 8 spots may be alternatively delivered by a modified apparatus.

It is preferred that a center of this circle be positioned coincident with the center of the pupil of the eye being treated. A pulsed holmium doped YAG laser, emitting radiation with a wavelength of about 2.13 microns, is utilized as the source. Each radiation spot has a diameter of about 600 microns. Treatment is accomplished, according to one specific set of parameters, by exposing the cornea to a series of from 5 to 15 radiation pulses, 10 pulses being used in one application. Each pulse has a duration of about 250 microseconds. The pulses are delivered at a rate of about 5 Hz. (about 200 milli-seconds between successive pulses).

The diameter of the circular spot pattern, the number of spots in the pattern being utilized and the amount of energy being delivered are selected to provide correction for different refractive errors. To correct for hyperopia, the cornea is exposed to all eight spots in a circle having a diameter within a range of about 5.5 to 8 mm., 6 mm. being typical, with an energy level of from 15–35 milli-joules (typically 25) being delivered to each spot per pulse. For correction of myopia, the spots are arranged in a circle having a diameter within a range of about 2 to 4 mm., 3.5 mm. being typical. Each of the eight spots is then provided with from 12–25 milli-joules (typically 20) of energy. Alternatively, the cornea can be exposed in its center, for myopia correction, to a single spot or pattern of spots to produce corneal flattening to some predetermined shape.

In the case of correcting for regular astigmatism, only 4 spots of the larger (5.5 to 8 mm.) are used in two opposing quadrants (the other 4 spots being blocked), with the pattern being rotated to position the spots symmetrically with the flattest meridian of the cornea's outside surface. This treatment will remove a cylindrical error of refraction from the eye. Other patterns are used to correct for irregular astigmatism. It is preferred, with patients having both spherical errors (hyperopia or myopia) and astigmatism, to first correct the eye for the astigmatism and then expose it again to the complete pattern in order to correct for the spherical error.

The parameter ranges given in the immediately preceding paragraph have been used with the system of copending application Ser. No. 07/923,813 without the use of a contact lens or other heat removal material in contact with the cornea. The spot pattern is projected onto the cornea without contact with the cornea. When a contact lens is used, the energy levels given above are increased by a few percent to compensate for Fresnel losses at surfaces of the contact lens through which the radiation pattern passes. In either case, the purpose of the treatment is to raise the temperature within volumes of the stroma positioned behind the radiation pattern to within a range of 58–75 degrees Celsius. Collagen tissue within such volumes thus shrinks and causes the outside surface of the cornea to be reshaped.

It is essential to understand that one of the primary advantages enjoyed by the practice of this invention is the noninvasive nature of the application process and the fact that no substantial wound-healing response is produced in the cornea. Although the changes to the corneal shape and curvature are long-term physical changes, there are controls in place that prevent the likelihood of there being any risk whatsoever to the patient. It is important to note that the viability of the corneal endothelium, a delicate and critical layer to human eye sight, together with other essential visual components of the eye are maintained throughout the procedure.

EXAMPLE

The following example of an animal procedure on a New Zealand white rabbit was performed to demonstrate the method required to correct myopia by flattening the central anterior surface of the cornea in an axisymmetric pattern with its origin on the central visual axis. Other procedures have also been performed to demonstrate the methods required to correct hyperopia by steepening the central anterior surface of the cornea in a like axisymmetric pattern and to correct astigmatism by unsymmetric treatment so as to produce different values of corneal flattening and/or steepening along different meridians of the cornea.

Following administration of a general anaesthetic, the rabbit was placed on a small table that included a head mount and positioner for accurate alignment of diagnostic instruments and for accurate delivery of a hydrogen fluoride chemical laser beam (from a modified Helios Inc. chemical laser system equipped with a diffraction grating for tuning output wavelength) onto the rabbit cornea. The table is mobile, permitting it to be moved from the laser treatment area to each of several diagnostic instrument stations while the rabbit head and eye are kept in the proper orientation for either laser delivery or diagnostic measurements.

Prior to laser treatment, several pre-treatment measurements were made on both eyes of the rabbit. First the corneal thicknesses were determined using a DGH Technology, Inc. Model DGH500 ultrasonic pachymeter. Next, the corneas of both eyes were viewed through a Zeiss slit lamp microscope to determine that the corneas were smooth and free of surface defects. Then, just prior to laser treatment, the curvatures of the anterior corneal surfaces were determined with an International Diagnostic Instruments, Ltd. Corneascope. Several post-laser treatment measurements of corneal curvature were made using either the Corneascope or an EyeSys Corneal Analysis System. The former instrument produces a Polaroid film record that must be analyzed manually at a later time while the latter instrument utilizes a video camera and computer analysis system to yield near-realtime corneal topography maps. Both instruments provide sufficiently precise corneal curvature measurements to determine the effectiveness of the corneal reshaping procedure.

For laser treatment, the rabbit was positioned so that the eye to be treated was the correct distance from a focussing lens to produce a predetermined laser beam spot size on the cornea. The hydrogen fluoride (HF) chemical laser was tuned by a diffraction grating to produce a single laser emission line; in this example, the HF $P_{1-0}(3)$ transition that lases at 2.608 μm wavelength was used. This predetermined wavelength has been verified in separate infrared spectroscopic measurements on human corneas to provide a correct optical penetration depth of ca. 90 μm to treat anterior stromal collagen tissue. Accurate power and irradiance distribution measurements of the laser beam were obtained to permit determination and adjustment of the laser beam irradiance so as to generate the predetermined irradiance for treatment. The laser beam power incident on the rabbit cornea was approximately 1.0 W. The laser beam spot size was approximately 500 μm diameter, leading to an average irradiance of approximately 500 W/cm$^2$. This spot was slewed in the annular pattern illustrated in FIG. 9. The diameter of the center of the annulus was 4 mm and the annulus was positioned axisymmetrically around the central visual axis. An X-Y scanner (General Scanning Model gs/EYE optical scanner) was used to slew the beam at a predetermined slew rate so that the complete annular pattern was generated in a predetermined time of 200 milliseconds (ms). An optical shutter was synchronized to permit delivery of only a single annulus on the anterior surface of the cornea. The total delivered energy was 200 millijoules (mJ).

Immediately following treatment, measurements of corneal thickness and corneal topography were made. In addition, slit lamp photomicroscopy was performed to observe corneal changes. Similar measurements of corneal topography of both the treated and untreated (control) eyes were made at intervals following treatment over a period of 24 weeks. FIG. 10 shows the measured pre-laser and post-laser values of corneal refractive power for both the rabbit eyes. Note that the refractive (dioptric) power of rabbit eyes normally varies with time due to growth. Therefore, the refractive power of the control eye decreased approximately five diopters over the period of observation. This type of "baseline drift" is present in all non-adult rabbit eyes, including both the treated and untreated eyes of the example rabbit.

The change in corneal shape due to laser treatment is readily apparent in FIG. 10. The immediate post-laser treatment value of refractive power for the treated eye is approximately five diopters less than the pre-laser value, so the cornea has been flattened appreciably. At 4 weeks after treatment, FIG. 10 shows that some of the initial flattening has been reduced, but the treated eye has nearly three diopters lower refractive power than the control eye. The difference of three diopters central flattening persists at 10 weeks and at 24 weeks following treatment. This persistence of the central flattening is evidence that little or no wound-healing response that generates stromal regrowth and anterior corneal shape change has occurred.

Examination of slit lamp photomicrographs revealed that the epithelial layer of the treated cornea was damaged initially. Superficial whitening of the treated annulus was noted. This whitening cleared within a few days, leaving little or no "haziness" of the anterior surface. There have been no other complications of the procedure such as the recurrent erosions that have been observed by other workers who performed thermokeratoplasty on both animal and human patients.

Improved experiments have been carried out on in vitro eyes using a heat sink material to protect anterior corneal structures from thermal damage. Identical laser treatments have been applied to the same eye with, and without, a heat sink coupler in place. Predetermined functionally effective doses of light have been delivered using the hydrogen fluoride chemical laser source to demonstrate the effectiveness of the heat sink coupler in preventing damage to the corneal epithelium and the Bowman's layer while causing corneal reshaping to generate correction of myopia.

FURTHER FIBER OPTIC EMBODIMENTS

Referring to FIGS. 15 and 16, an optical fiber bundle 101, similar to the fiber optic array of the embodiment of FIGS. 2A and 11, has one end thereof attached to the surface 40 of the coupler 10 described above with respect to FIG. 13. As shown in FIG. 16, ends of the optical fibers of the bundle 101 are viewable through the coupler in a region inside of the vacuum ring. The illumination pattern across the cornea in contact with the coupler surface 30 is determined by directing the infra-red electromagnetic radiation along selected ones of the optical fibers from a diode laser array 103. That is, rather than scanning the fiberoptic array with a single diode laser, as described in the embodiments of FIGS. 2A and 11, a separate diode laser is coupled within the array 103 to each of the optical fibers within the bundle 101 at an end opposite of that to which the coupler 10 is attached. An electrical power supply circuit 105 individually provides a controlled amount of power to the selected diode lasers within the array 103 by interconnection over separate circuits 107. A microprocessor based controller 109 controls, through an interconnecting bus 111, which of the diode lasers in the array 103 are to be energized by the power supply 105. A user interface 113, preferably including a keyboard and monitor, allow the operator to configure the system for a particular corneal reshaping procedure by setting parameters within the controller 109. The controller 109 also controls a vacuum pump 115 that is mechanically connected to the vacuum port 21 of the coupler 10. The coupler 20 may be made to be removable from the fiber bundle 101, or the fiber bundle 101 may be made to be removable from the diode laser array 103, if desired. Either or both of the coupler 20 and the fiber bundle 101 may be made disposable.

The output frequency of radiation from commercially available diode lasers is dependent upon both their composition and operating temperature. Thus, it is desirable to control the temperature of the diode laser array 103, a temperature control circuit 117 being provided under the control of the controller 109 over a bus 119. Available diode lasers also exhibit a greater output power at lower temperatures, so cooling them is usually desirable. Optimally, each of the diode lasers within the array 103 is provided with its own individual cooling device that is separately controlled by a signal on one of a plurality of circuits 121 from the temperature control circuitry 117. Individual solid state thermo-electric coolers are preferably mounted as part of each diode laser within the array 103. The temperature of each diode laser is measured by a thermistor or thermocouple attached to the individual diode lasers within the array 103. Temperature signals are communicated to the temperature control circuitry 117 over circuits 121. A particular advantage of individually controlling the temperature of each diode laser within the array 103 is that the output wavelength can be controlled over a small range by setting, through the controller 109, the desired operating temperature of each of the diode lasers. This wavelength control allows compensation for wavelength differences caused by variations in composition of the materials forming each of the diode lasers. Further, it allows selecting, to some extent, the corneal absorption coefficient by selecting the wavelength at which each energized diode laser operates. That is, the temperature to which a volume of the cornea is raised by exposure to a given infra-red radiation spot can be controlled over at least a limited range by controlling the temperature of the diode laser generating that radiation spot. This allows the energy level of all the spots to be controlled to be the same, or, alternatively, to intentionally be made different in order to individually control the temperature profile through the thickness of the stroma at the location of each radiation spot. Very sophisticated corneal recurvature operations can be accomplished by such a method.

At the time of filing the present patent application, diode lasers having a sufficient power for this application are costly, thus making the implementation described with respect to FIGS. 15 and 16 very expensive. The complete flexibility provided by the system of FIGS. 15 and 16 comes at some substantial cost. Therefore, an alternative system embodiment shown in FIGS. 17, 18 and 19 utilizes a corneal coupler 125 of a different design and only few diode lasers, such as lasers 127, 129 and 131, as required to generate the separate number of spots. The individual spots may be circular or some other controlled shape. In the example system of FIGS. 17-19, eight such spots, and thus eight such diode lasers are employed. Each diode laser is coupled into one end of an optical fiber, such as the respective optical fibers 133, 135 and 137. Each of the diode lasers has one of respective thermo-electric coolers 139, 141 and 143 attached. Similarly, each of the diode lasers has one of respective thermistors or other temperature measuring devices 145, 147 and 149 attached. A temperature control circuit 151 receives the individual temperature dependent electrical signals from the diode laser thermistors, and generates a controlling electrical signal to the individual coolers in order to maintain the individual diode lasers at desired temperatures.

This thus allows a closed loop temperature control of each of the diode lasers in the system. A power control circuit 153 individually provides the correct amount of current to each of the diode lasers 127, 129 and 131. This power is set by a system controller 155. The system controller 155 also controls the temperature control circuitry 151 in order to operate the individual diode lasers at temperatures which provide the desired individual infrared radiation wavelength. A user interface 157, usually including a monitor and keyboard, allows the operator to program the system controller 155 for the desired temperature and input power to each of the diode lasers. Of course, some of the lasers will not be energized at all where a number of spots to be generated is fewer than the number of diode lasers in the system. The system controller 155 also controls a vacuum pump 159 that is connected to the coupler 125 through a vacuum line 161.

Rather than each of the optical fibers 133, 135, 137, etc., being fixedly attached to the coupler 125, each of the diode laser illuminated fibers in the system are removably attached to a backside of the coupler 125 in a manner shown best in the views of FIGS. 18 and 19. This allows easy replacement of the coupler without having to make any other physical changes to the rest of the system shown in FIG. 17. Alternatively, but not preferably, the optical fibers can be permanently attached to the coupler and a multi-fiber connector provided for disconnecting the coupler/fibers from the rest of the system in order to replace it. In either case, the coupler can be made to be a disposable item.

The coupler 125 is formed of two primary components. A first component is a transparent heat sink element 163 that has a concave surface 165 shaped to contact an anterior surface of a cornea being treated. A circular groove 167 is provided around the outside edge of the surface 165 in order to hold the coupler 125 against the cornea being treated when a vacuum is applied to the groove 167. A plurality of ports spaced around the element 163 could alternatively be provided. The groove 167, or such ports, are coupled with the vacuum line 161. However, some ophthalmologists and other operators may prefer not to use such a vacuum attachment system but rather will simply hold the coupler 125 by hand against the eye during the radiation exposure. Application of sufficient pressure between the surface 165 and the eye prevents movement of the eye during the short period of treatment.

The material of the element 163 is preferably made of the aforementioned Poly IR5 fluoro-polymer material or Infrasil quartz. Its thickness is preferably substantially uniform. These materials have thermal transfer properties sufficient to carry heat away from the anterior surface of a cornea to which it is attached in order to provide the temperature profile through the cornea thickness that has been described earlier. These materials are also sufficiently non-absorptive of infra-red radiation treatment wavelengths of around two microns that radiation loss and a resulting heating of the element 163 is avoided. The preferred materials are also substantially transparent to visible radiation wavelengths.

Attached to an outer curved surface of the first element 163 is a second element 169 having a complementary shape at a surface that adjoins and is fixed to the outer surface of the contact lens element 163. A primary purpose of the element 169 is to provide properly positioned receptacles for each of the optical fibers that are to be connected to it for the delivery of energy to the cornea. Alternative devices and structures could instead be provided on the backside of the element 163 to position and hold the optical fiber ends in desired spaced apart pattern but what is shown in FIGS. 17-19 is preferred. A circular pattern of eight fiber receiving receptacles is best shown in the backside view of FIG. 18, including passages 171 and 173 that are also shown in a cross sectional view of FIG. 19. The pattern of passages is formed to correspond with the radiation pattern to which the cornea is desired to be exposed. In the example of FIG. 17-19, eight such passages are equally spaced around a circle having a center 175, similar to the patterns previously described to be generated with the non-contact system of copending application Serial No. 07/923,813. Other parameters, however, are likely to be different, as described below.

As illustrated in FIG. 19, each of the optical fibers removably connected with the coupler 125 has a coupler attached to its free end. For example, the optical fiber 133 is terminated in a circularly shaped sleeve 177. The fiber 133 with its outer sheath attached is firmly fit within an opening interior of the sleeve 177. An enlarged diameter portion of the sleeve 177 is provided for ease in gripping by hand. A second sleeve 179 is attached around the outside of the optical fiber 133 along a distance removed somewhat from its end. The sleeve 177 extends over the second sleeve 179 for a distance to provide the enlarged diameter portion for gripping. The second sleeve 179 also provides additional support and stiffening of the optical fiber 133 for a distance adjacent to its end. A portion 181 of the optical fiber, with sheath removed, is exposed in the interior passageway of the sleeve 177. An end of the fiber tip 181 is maintained a controlled distance inward of an extreme end 182 of the sleeve 177, which extreme end 182 abuts against the outer surface of the contact lens element 163. Since the infra-red energy exits the end 181 of the optical fiber in a spreading cone, this distance significantly affects the size of the resulting spot which is illuminated on the cornea surface. It is most convenient when this distance be made to be the same for each of the optical fiber ends. Since the optical path length from each of the optical fiber ends to the cornea surface is made to be substantially the same, the size of each spot is thus substantially the same.

The system is preferably calibrated to make the size, energy distribution and total energy of each spot substantially the same. Of course, the infra-red radiation spots can intentionally be made to have any of these aspects different from one-another, if desired for some reason. For example, the spot sizes can be made to have different sizes by simply providing different distances between the ends of the optical fibers and the open ends of their respective sleeves. However, use of the system then becomes somewhat more involved.

Each of the optical fiber free ends fitted with the structure described for that of the optical fiber 133 can be held within the second optical element 169 in any one of a number of different ways. The simplest way is to size the mating element portions so that a tight frictional fit is obtained upon hand insertion of the fiber tip sleeve into the receiving aperture of the element 169. If more positive control is required, a set screw (not shown) can be added for each of the optical fibers in individual holes extending inward from a side edge of the element 169. Alternatively, available latching mechanisms can be adapted for the small size of the optical fiber sleeves and receiving apertures.

Since the treatment radiation does not pass through the second element 169, its properties with respect to infra-red radiation are not important. But it is important that the element 169 be substantially transparent to visible wavelengths so that the operator may properly position it on the patient's cornea before affixing it to the cornea by applying vacuum to the vacuum line 169. The material of the element 169 should also be easy to work in order to form it into the shape with apertures as described. Commercially available plexiglass is among satisfactory materials for this purpose.

It is preferred, as shown in FIG. 19, that the fibers be oriented substantially perpendicularly with the surface 165, and thus also with the similarly shaped anterior surface of the cornea being treated. This results in a central ray of cone shaped infrared energy exiting an end of the individual optical fibers striking the cornea perpendicularly. Another way to express this geometry is that a longitudinal axis of each of the apertures in the element 169, and thus of each of the optical fibers inserted therein, passes through a center of curvature of the surface 165 in a region opposite to an inner end of the aperture and termination of the fiber positioned therein.

An advantage of the treatment system of FIGS. 17–19 is that many versions of the coupler 125 may be kept on hand and easily interchanged. Different versions can be provided for different treatments. For example, the apertures may be positioned in a circle of different diameters in two different couplers, about 6 mm. for effecting correction of hyperopia and about 3.5 mm. for correction of myopia. If only spherical correction is to be effected, optical fibers are then inserted into each of the 8 apertures and energized. If cylindrical correction is to be accomplished, optical fibers need be inserted only into the 4 apertures of two opposing quadrants and then energized, the remaining apertures being unfilled. More complicated astigmatic correction may require yet a different pattern of apertures. Even some spherical correction treatments may desirably be performed with a coupler having optical fiber receiving apertures arranged in two circles of different diameters. In all these cases, the operator can see through the coupler element 125 in order to line up the center 175 of the coupler with a center of the pupil of the eye being treated. Some treatments may benefit from a two or more exposures though all connected fibers with the coupler rotated about its center 175 in between exposures after the vacuum is released.

For the convenience of the operator, the element 169 may have an alignment pattern inscribed on one of its surfaces. A series of concentric circles makes it easier to center the coupler with the pupil of the eye being treated. A series of lines or other marks across the coupler at various angles through the center 175 makes it easier to orient the coupler by rotation when a non-spherical correction, such as for astigmatism, is being made.

In all cases described herein of a coupler being attached to a corneal anterior surface, a tear layer will almost always be interposed therebetween. It is desirable, however, to minimize the thickness of any tear layer, at least in the regions through which radiation passes. This is in order to minimize the amount of radiation absorption by any such layer since such absorption reduces the amount of energy that remains available to heat the stromal collagen. However, it is generally desired to minimize such a layer which is accomplished by shaping the corneal contacting surface 165 of the coupler as closely as possible to the outside surface of the eye being treated.

In the embodiments described above, the cornea is exposed to a pattern of circular spots. It is certainly possible, of course, to expose the cornea to lines, arcs, or other radiation patterns other than simple circular spots. The embodiment of FIGS. 15 and 16, for example, can form such other shapes from a plurality of contiguous dots formed from exposing a selected pattern of a plurality of contiguous optical fibers to the infrared treatment radiation. In the embodiment of FIGS. 17–19, optical elements can be formed at the ends of each of the optical fibers in order to project into the cornea some shape other than a round spot. Further, a number of fibers can be positioned adjacent to one another in the embodiment of FIGS. 17–19 in order to form other radiation patterns.

The preferred diode laser for use in the embodiments described above is an indium-gallium-arsenide-phosphide (InGaAsP) type formed in a strained layer with a double quantum well. Such a diode laser, commercially available from Applied Optronics Corp. of South Plainfield, N.J., is selected to emit electromagnetic radiation within a range of about 1.9 to 2.1 microns, depending upon the specific composition and operating temperature. Within this range, a wavelength of about 1.95 microns corresponds to the maximum absorption by the stromal tissue which is patterned after that of water, while a wavelength of about 2.1 microns corresponds to the minimum tissue absorption within the diode laser's available range of wavelengths. The difference in absorption is a factor of about 4. Thus, there is a considerable amount of control available over the radiation absorption characteristics by selection of the composition of the diode laser and by controlling its operating temperature, thus to control the thermal profile through the thickness of the stroma in exposed areas.

Such diode lasers are preferably operated by applying a single pulse of radiation lasting from 200 to 400 milliseconds. When operating at about 1.95 microns, the energy applied is preferably within a range of from 15 to 35 milli-joules per approximately 600 micron diameter spot, 25 milli-joules being typical. At this wavelength, only about one tenth of the total energy is required as compared with the pulsed holmium laser embodiment described previously. This is because of the different wavelengths used and delivery of the radiation in a single pulse rather than a series of repetitive pulses. When operating at about 2.1 microns, approximately four times the amount of energy is required. Either way, heat affected zones within the stroma are raised to within the treatment range of from 58 to 75 degrees Celsius in order to effect corneal recurvature. Such zones will be deeper into the stroma when the less absorptive wavelengths are used.

By use of a separately controlled diode laser to generate each spot or other shaped area to which the cornea is exposed, the duration of the exposure pulse forming each exposed area may be individually controlled in addition to controlling the degree to which the radiation is absorbed by the corneal tissue through adjustments of its wavelength. This flexibility is particularly advantageous for correction of non-spherical refractive errors, such as astigmatism.

Although the examples of tissue shrinkage given above relate specifically to refractive error correction of the eye, very similar procedures, couplers and systems can be employed to shrink or otherwise treat tissue in other regions of the human body. In any such treatment, the surface of the coupler contacting a surface of the body, either an external or an internal surface, is shaped to closely conform to the shape of such a surface in order to provide maximum coupling of the infra-red treatment radiation. The infra-red radiation patterns, specific wavelength(s), energy applied, manner of applying the energy, and other parameters, are selected consistent with the particular tissue treatment.

The selective energization or positioning of optical fibers to generate desired radiation patterns is not limited to use of a contact coupler. An example of non-contact treatment is given in FIG. 20. A plurality of optical fibers 201 form a desired infra-red radiation pattern at a surface 203 that is imaged by an appropriate optical system onto a surface 207 of a cornea or other body portion to be treated. The plurality of fibers 201 can be a complete bundle, such as the bundle 101 (FIGS. 15 and 16), wherein those fibers creating the desired pattern in the surface 203 are illuminated from their opposite ends. Alternatively, the plurality of fibers 201 can be a few fibers whose ends are positioned into the desired pattern, as done in the embodiment of FIGS. 17-19.

Although the preferred embodiment of the apparatus and method of this invention has been described here and above in some detail, it should be appreciated that a variety of embodiments will be readily apparent to those skilled in the art. The description of the apparatus and method of this invention is not intended to be limiting on this invention but is merely illustrative of the preferred embodiments of this invention. Other apparatus and components and variations on the method which incorporate modifications or changes to that which have been described herein are equally included within this application.

What is claimed is:

1. A system for internally heating human tissue by exposing an outside surface of a given shape to one of at least first and second predetermined and distinct patterns of infra-red radiation, comprising:

at least first and second radiation couplers that each have on one side thereof a first surface with a shape that is complementary to said given outside surface shape and a second surface on an opposite side thereof, each of said at least first and second couplers having a plurality of apertures spaced apart across said second surface and extending into said second surface to closed ends within the coupler a distance from said first surface, at least regions of each of said at least first and second couplers between said closed ends of the plurality of apertures and said first surface being substantially transparent to said infra-red radiation, said first coupler having said aperture ends thereof arranged across said first surface in said first predetermined pattern, and said second coupler having said aperture ends thereof arranged across said first surface in said second predetermined pattern, a source of said infra-red radiation, and a plurality of optical fibers having first and second ends, said first ends being coupled to receive infra-red radiation from said source and said second ends having individual sleeves attached thereto which are shaped to mate with at least one aperture of each of said at least first and second couplers and allow insertion of the sleeves into said at least aperture in a manner to self-align the individual optical fiber second ends to which the sleeves are attached with the closed end of said at least one aperture, thereby to allow said at least one of said second optical fiber ends to be removably inserted into at least one of the apertures of each of said first or second couplers, said optical fiber sleeves securely fitting in said apertures without allowing adjustment of the position of the optical fiber second ends in a direction across said first surface.

2. The system of claim 1 wherein said first element includes a material within a group consisting of quartz, calcium fluoride, sapphire, diamond and a fluoro-polymer.

3. The system of claim 1 wherein said first surface of each of the first and second couplers is in a concave shape.

4. The system of claim 1 wherein the apertures of each of the first and second couplers are arranged in a circle across said second surface.

5. The system of claim 1 which additionally comprises a vacuum pump and wherein each of said first and second couplers includes an opening in said first surface that is connectable to said vacuum pump.

6. The system of claim 1 wherein each of said first and second couplers comprise a first element including said first surface and a second element including said second surface, said first and second elements being attached to each other along a third surface that is intermediate of said first and second surfaces, said plurality of apertures extending completely through the second element but not into the first element, thereby locating said aperture ends at said third surface.

7. The system of claim 6 wherein at least regions within the first element that are located opposite said aperture ends are transparent to said infra-red radiation and are of the same thickness, and further wherein at least some of said second optical fiber ends have a hollow sleeve attached with one end thereof remaining open and positioned a certain distance removed beyond said optical fiber end.

8. The system of claim 6 wherein said second element is solid except for the apertures therein, said apertures and said optical fiber sleeves each having mating cross-sectional shapes that allows the optical fiber sleeves to be moved with respect to the second element only within said apertures in a direction substantially perpendicular to said first surface.

9. A method of reshaping outside surfaces of first and second corneas by selectively shrinking regions of stromal tissue therewithin according to first and second distinct patterns thereacross, comprising:

providing a source of electromagnetic radiation of a wavelength that is absorbed by stromal tissue of the first and second corneas, providing a plurality of optical fibers having free ends, providing first and second couplers that each have a surface with a shape that is complementary to a respective one of the outside surfaces of the first and second corneas and optical fiber free end receiving apertures extending into backsides thereof across the corneal contact surfaces according to said first and second patterns, inserting the free ends of at least some of the optical fibers into individual ones of the apertures of said first coupler, positioning the first coupler corneal contact surface against the first cornea, directing electromagnetic radiation from the source along said at least some of the optical fibers in a manner to heat regions of stromal tissue therein sufficient to shrink the tissue according to said first pattern and thereby reshape the outside surface of the first cornea, removing the first coupler from the first cornea, removing the free ends of said at least some of the optical fibers from the apertures of the first coupler, inserting the free ends of said at least some of the optical fibers into individual ones of the apertures of said second coupler, positioning the second coupler corneal contact surface against the second cornea, directing electromagnetic radiation from the source along said at least some of the optical fibers in a manner to heat regions of stromal tissue therein sufficient to shrink the tissue according to said second pattern and thereby reshape the outside surface of the second cornea, removing the second coupler from the second cornea, and removing the free ends of said at least some of the optical fibers from the apertures of the second coupler.

\* \* \* \* \*

UNITED STATES PATENT AND TRADEMARK OFFICE
CERTIFICATE OF CORRECTION

PATENT NO. : 5,779,696
DATED : July 14, 1998
INVENTOR(S) : Michael J. Berry, et al.

It is certified that error appears in the above-identified patent and that said Letters Patent is hereby corrected as shown below:

On the Title Page, [73] Assignee, replace:
"[73] Assignee: Sunrise Technologies International, Inc., Fremont, Calif."

with

--[73] Assignee: Laser Biotech, Inc., Fremont, Calif.--

Signed and Sealed this

Sixteenth Day of March, 1999

Attest:

Q. TODD DICKINSON

*Attesting Officer*    *Acting Commissioner of Patents and Trademarks*